(12) United States Patent
Seeger et al.

(10) Patent No.: US 12,054,708 B2
(45) Date of Patent: Aug. 6, 2024

(54) PROTEIN SCREENING AND DETECTION METHOD

(71) Applicant: Universität Zürich, Zurich (CH)

(72) Inventors: Markus Seeger, Thalwil (CH); Pascal Egloff, Thalwil (CH); Iwan Zimmermann, Zurich (CH)

(73) Assignee: Universität Zürich, Zurich (CH)

( * ) Notice: Subject to any disclaimer, the term of this patent is extended or adjusted under 35 U.S.C. 154(b) by 601 days.

(21) Appl. No.: 16/345,895

(22) PCT Filed: Oct. 30, 2017

(86) PCT No.: PCT/EP2017/077816
§ 371 (c)(1),
(2) Date: Apr. 29, 2019

(87) PCT Pub. No.: WO2018/078167
PCT Pub. Date: May 3, 2018

(65) Prior Publication Data
US 2019/0276819 A1   Sep. 12, 2019

(30) Foreign Application Priority Data
Oct. 31, 2016  (EP) .................................... 16196571

(51) Int. Cl.
*C12N 15/10* (2006.01)
*C07K 16/12* (2006.01)
*G01N 33/68* (2006.01)

(52) U.S. Cl.
CPC .......... *C12N 15/1065* (2013.01); *C07K 16/12* (2013.01); *C12N 15/1034* (2013.01);
(Continued)

(58) Field of Classification Search
CPC ................ C07K 16/12; C07K 2317/22; C07K 2317/569; C07K 2319/21; C07K 2319/22;
(Continued)

(56) References Cited

U.S. PATENT DOCUMENTS 11,339,434 B2 *   5/2022   de Raad ............... G01N 33/573
2009/0233806 A1 *  9/2009   Carr .................... G01N 33/6845
                                                              506/9

FOREIGN PATENT DOCUMENTS

EP   1647600   4/2006
EP   2436766   4/2012
(Continued)

OTHER PUBLICATIONS

Sadygov et al. (Nature Methods, 2004, vol. 1, No. 3, pp. 195-202) (Year: 2004).*
(Continued)

*Primary Examiner* — Jeremy C Flinders
(74) *Attorney, Agent, or Firm* — Knobbe, Martens, Olson & Bear, LLP

(57) ABSTRACT

The invention relates to a method for identifying and quantifying a polypeptide from a library of polypeptides. The method comprises the steps of: 1—providing a polypeptide library and a detection tag library, 2—generating a nested library comprising the polypeptides and the detection tags, 3—sequencing the nested library, 4—selecting a member of the nested library in one or several selection steps that are independent of a physical genotype-phenotype linkage, 5—isolating the detection tag from the selected polypeptide, 6—identifying and quantifying the detection tag by mass spectrometry, 7—obtaining the sequence of the selected polypeptide. The invention also relates to a collection of
(Continued)

polypeptides, a collection of detection tags, and a collection of plasmid vectors.

20 Claims, 8 Drawing Sheets

Specification includes a Sequence Listing.

(52) U.S. Cl.
CPC ..... *C12N 15/1093* (2013.01); *G01N 33/6845* (2013.01); *G01N 33/6848* (2013.01); *C07K 2317/22* (2013.01); *C07K 2317/569* (2013.01); *C07K 2319/20* (2013.01); *C07K 2319/21* (2013.01); *C07K 2319/22* (2013.01); *C07K 2319/23* (2013.01); *C07K 2319/24* (2013.01); *C07K 2319/41* (2013.01); *C07K 2319/43* (2013.01); *C12Q 2563/119* (2013.01); *C12Q 2563/185* (2013.01)

(58) Field of Classification Search
CPC ............ C07K 2319/23; C07K 2319/24; C07K 2319/41; C07K 2319/43; C12N 15/1065; C12N 15/1093; C12Q 2563/119; C12Q 2563/185; C12Q 2563/186; G01N 33/6845; G01N 33/6848
See application file for complete search history.

(56) References Cited

FOREIGN PATENT DOCUMENTS

| WO | WO 97/07132 | 2/1997 |
| WO | WO 00/31115 | 6/2000 |
| WO | WO 00/57183 | 9/2000 |
| WO | WO 2004/011676 | 2/2004 |
| WO | WO 2007/134327 | 11/2007 |
| WO | WO 2009/036157 | 3/2009 |
| WO | WO 2014/139130 | 9/2014 |

OTHER PUBLICATIONS

Levy et al. (Annu. Rev. Genom. Hum. Genet., (2016) 17:95-115)) (Year: 2016).*
Kimple Michelle et al., "Overview of affinity tags for protein purification" Current protocols in protein science, Sep. 24, 2013, vol. 73.
Hernan Ron et al. "Multiple epitope tagging of expressed proteins for enhanced detection" Biotechniques Rapid Dispatches, Informa Healthcare, US, vol. 28, No. 4, Apr. 1, 2000, pp. 789-793.
Zimmermann et al.: "Synthetic single domain antibodies for the conformational trapping of membrane proteins", www.biorxiv.org/content/early/2017/07/26/168559, Jul. 26, 2017, in 62 pages.
International Search Report for International Application No. PCT/EP2017/077816, Mar. 20, 2018 in 5 pages.
Mass spectrometry—Wikipedia, https://en.wikipedia.org/wiki/Mass_spectrometry, pp. 1-25, retrieved on May 19, 2023.

* cited by examiner

A Immobilization of pool members in complex with biotinylated target at two columns, followed by off-rate selection A | 1. *In vitro* display (Generating a pool of binder candidates)

B Strain-specificity readout

SEQUENCE LISTING

<160> NUMBER OF SEQ ID NOS: 5

<210> SEQ ID NO 1
<211> LENGTH: 2
<212> TYPE: PRT

```
<213> ORGANISM: Artificial Sequence
<220> FEATURE:
<223> OTHER INFORMATION: tag sequence

<400> SEQUENCE: 1

Trp Arg
1

<210> SEQ ID NO 2
<211> LENGTH: 3
<212> TYPE: PRT
<213> ORGANISM: Artificial Sequence
<220> FEATURE:
<223> OTHER INFORMATION: tag sequence

<400> SEQUENCE: 2

Trp Leu Arg
1

<210> SEQ ID NO 3
<211> LENGTH: 4
<212> TYPE: PRT
<213> ORGANISM: Artificial Sequence
<220> FEATURE:
<223> OTHER INFORMATION: tag sequence

<400> SEQUENCE: 3

Trp Gln Ser Arg
1

<210> SEQ ID NO 4
<211> LENGTH: 5
<212> TYPE: PRT
<213> ORGANISM: Artificial Sequence
<220> FEATURE:
<223> OTHER INFORMATION: tag sequence

<400> SEQUENCE: 4

Trp Leu Thr Val Arg
1               5

<210> SEQ ID NO 5
<211> LENGTH: 6
<212> TYPE: PRT
<213> ORGANISM: Artificial Sequence
<220> FEATURE:
<223> OTHER INFORMATION: tag sequence

<400> SEQUENCE: 5

Trp Gln Glu Gly Gly Arg
1               5
```

PROTEIN SCREENING AND DETECTION METHOD

RELATED APPLICATIONS

This application is the U.S. National Stage under 35 U.S.C. § 371 of International Application No. PCT/EP2017/077816, filed Oct. 30, 2017, which claims the benefit of European Provisional Application No. 16196571.0, filed Oct. 31, 2016, the entire contents of each of which is incorporated in its entirety by reference herein.

A Sequence Listing submitted as an ASCII text file via EFS-Web is hereby incorporated by reference in accordance with 35 U.S.C. § 1.52(e). The name of the ASCII 15 text file for the Sequence Listing is RENP029_001APC_ST25.txt, the date of creation of the ASCII text file is Aug. 1, 2019, and the size of the ASCII text file is 911 bytes.

The present invention relates to a method of attaching detection tags to a protein library and to subsequently use the tags to identify and quantify proteins that fulfil defined biophysical or pharmacological criteria.

BACKGROUND

Protein screens and protein display methods are state of the art methods to identify or enrich proteins that exhibit certain characteristics (e.g. high affinity binding to a target molecule).

In screens, proteins are analyzed one by one. This is very laborious and limited to a comparatively low number of tests. In a screen for binding proteins for example, individual binder candidates are identified by ELISA, and positive ELISA hits are characterized further, e.g. they are biophysically characterized by size exclusion chromatography, unfolding experiments and their therapeutic potential is tested in vivo in animal models.

In display methods, entire protein pools (originating from libraries) are enriched over several selection rounds. Processing of pools allows for an enormous throughput without much labour. Display methods such as phage, ribosome or yeast display, however, require a physical linkage between the phenotype (the protein) and the genotype (its encoding nucleic acids). This is a severe limitation for most analyses, because the physical entities required for conducting the display (i.e. the phage, the ribosome and the encoding DNA or RNA) are typically more than 100-fold larger than the actual binding molecule (e.g. an antibody fragment). This inevitably causes selection bias and restricts the possible selection pressures to a small subset of imaginable selections pressures—only selection pressures that are not critically affected by the enormous size of the display particle can be applied currently (e.g. binding).

Based on the above mentioned state of the art, the objective of the present invention is to provide means and methods for the identification of individual proteins fulfilling defined biophysical or pharmacological criteria from entire protein libraries in the absence of a physical genotype-phenotype linkage. This objective is attained by the claims of the present specification.

Terms and Definitions

The skilled person is aware that within the present specification, a number indicating the size of a library relates to the diversity of library members. A library I that is larger than a library II corresponds to a library I that comprises a higher number of unique library members than library II. A nucleic acid library with 100.000 members may comprise several millions of nucleic acid molecules, but only 100.000 distinct library members each characterized by a nucleic acid sequence unique within said library. Similarly, a polypeptide library with 1.000 members may comprise millions of polypeptide molecules, but only 1.000 unique polypeptide library members. The expression "one member of a library" relates to one particular library member which may be present in a plurality of identical copies.

Within the context of the present specification, the expression "two nucleic acid sequences are in frame" means that the number of base pairs between the last codon of the first nucleic acid sequence and the first codon of the second nucleic acid sequence is divisible by three.

Within the context of the present specification, the expressions "polypeptide is associated with detection tag", respectively "polypeptide/detection tag is associated with affinity tag" means that both aforementioned members are comprised within one primary amino acid sequence, i.e. one continuous polypeptide chain. Particularly, said detection tag and said polypeptide may be separated by one or more amino acids). Said detection tag and said affinity tag may also be separated by one or more amino acids.

Within the context of the present specification, the term "severable element" relates to a peptide sequence amenable to severing by chemical agents or by enzymatic means, e.g. by proteases. The proteases may be sequence specific (e.g. thrombin) or have limited sequence specificity (e.g. trypsin). The severable elements I and II may also be comprised within the amino acid sequence of the detection tag or the polypeptide, particularly in instances where the last amino acid of the detection tag or the polypeptide is a K or R.

Within the context of the present specification, the term "affinity tag" relates to a moiety attached to a polypeptide to enable purification of said polypeptide from a biochemical mixture. The purification (affinity purification) is based on a highly specific interaction (with a dissociation constant $\leq 10 E-5$) between the affinity tag and a binding partner of the affinity tag. Affinity tags may consist of an amino acid sequence, or may comprise an amino acid sequence to which a chemical moiety is attached by posttranslational modification. By way of non-limiting example, the affinity tag is selected from the group comprising a His-tag, a CBP-tag (CBP: calmodulin binding protein), a CYD-tag (CYD: covalent yet dissociable NorpD peptide), a Strep-tag, a StrepII-tag, a FLAG-tag, a HPC-tag (HPC: heavy chain of protein C), a GST-tag (GST: glutathione S transferase), an Avi-tag, a biotinylation tag, a Myc-tag, a 3×FLAG tag and a MBP-tag (MBP: maltose binding protein). Further examples of affinity tags can be found in Kimple et al., Curr Protoc Protein Sci. 2013 Sep. 24; 73:Unit 9.9.

Within the context of the present specification, the term "deep sequencing" relates to parallel sequencing of several thousand different nucleic acid molecules with a coverage of $\geq 5\times$, in particular $\geq 40\times$. The term "coverage" relates to the number of times a given nucleotide is read during the deep sequencing process on average.

In the context of the present specification, the term antibody is used in its meaning known in the art of cell biology and immunology. A whole antibody is a glycoprotein comprising at least two heavy (H) chains and two light (L) chains inter-connected by disulfide bonds. Each heavy chain is comprised of a heavy chain variable region (VH) and a heavy chain constant region (CH). Each light chain is comprised of a light chain variable region (abbreviated herein as VL) and a light chain constant region (CL). The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

Within the context of the present specification, the term "nanobody" relates to a "single domain antibody", i.e. an antibody fragment consisting of a single variable antibody domain. A nanobody is able to bind selectively to a specific antigen. It has a molecular weight of only 12-15 kDa (Harmsen et al., Appl. Microbiol. Biotechnol. 77 (1): 13-22). Usually, nanobodies are obtained by immunization of dromedaries, camels, llamas, alpacas or sharks with the desired antigen and subsequent isolation of the mRNA coding for heavy-chain antibodies. Nanobodies can be also be derived from common murine or human IgG with four chains.

Within the context of the present specification, the term "sybody" relates to a synthetic nanobody. Sybodies are not obtained via immunization with an antigen but selected in vitro from a synthetic library.

Within the context of the present specification, the term "enrichment" relates to a process of increasing the relative amount of a certain compound within a mixture of compounds.

Within the context of the present specification, the term "Flycode library" relates to an amino acid sequence library according to the invention, comprising a plurality of sequence variants.

Within the context of the present specification, the term "NestLink" relates to a method in which detection tags are attached to a protein library. Subsequently, the tags are used to identify and quantify individual proteins that fulfil defined biophysical or pharmacological criteria within the library. NestLink combines key benefits of screens and display procedures.

Within the context of the present specification, the term "hydrophobicity value" relates to a predicted value characterizing a peptide. The hydrophobicity value is calculated by the method described in Krokhin et al., Mol Cell Proteomics. 2004 September; 3(9):908-19, according to the formulas:

$$H = K_L * (\Sigma R_c + 0.42 R^1_{cNt} + 0.22 R^2_{cNt} + 0.05 R^3_{cNt}) \text{ if } H < 38$$

and $$H = K_L * (\Sigma R_c + 0.42 R^1_{cNt} + 0.22 R^2_{cNt} + 0.05 R^3_{cNt}) - 0.3 (K_L * (\Sigma R_c + 0.42 R^1_{cNt} + 0.22 R^2_{CNt} + 0.05 R^3_{cNt}) - 38) \text{ if } H \geq 38;$$

if $H < 38$, $H_{final} = H$;
if $H \geq 38$, $H_{final} = H - 0.3*(H-38)$;

where $H_{final}$ is the hydrophobicity value and $R_c$ are retention coefficients characteristic for amino acid types according to the following table:

| | $R_c$ |
|---|---|
| Trp | 11 |
| Phe | 10.5 |
| Leu | 9.6 |
| Ile | 8.4 |
| Met | 5.8 |
| Val | 5 |
| Tyr | 4 |
| Ala | 0.8 |
| Thr | 0.4 |
| Pro | 0.2 |
| Glu | 0 |
| Asp | −0.5 |

-continued

| | $R_c$ |
|---|---|
| Cys | −0.8 |
| Ser | −0.8 |
| Gln | −0.9 |
| Gly | −0.9 |
| Asn | −1.2 |
| Arg | −1.3 |
| His | −1.3 |
| Lys | −1.9 |

$R_{cNT}$ of an amino acid X is defined as:

$$R^x_{cNt} = (\Sigma R_c/20) - R^x_c$$

N corresponds to the residue number of the detection tag starting with 1 from the N-terminus. $K_L$ is defined as:

if $N < 10$, $K_L = 1 - 0.027*(10-N)$ if $N > 20$, $K_L = 1 - 0.014*(N-20)$ otherwise $K_L = 1$.

Amino acid sequences are given from amino to carboxyl terminus. Capital letters for sequence positions refer to L-amino acids in the one-letter code (Stryer, Biochemistry, 3rd ed. p. 21).

DETAILED DESCRIPTION OF THE INVENTION

Method for Selecting a Polypeptide from a Library of Polypeptides

According to a first aspect, a method for selecting a polypeptide from a library of polypeptides is provided. The method comprises the following steps:

a. A first nucleic acid library is provided. Each member of the first nucleic acid library comprises a polypeptide-encoding sequence encoding a member of a first polypeptide library. Each member of the first nucleic acid library is different from any other member of the first nucleic acid library.

b. A second nucleic acid library is provided. The second library comprises a plurality of members. Each member comprises a tag-encoding sequence encoding a detection tag. Each detection tag has the following characteristics:
  i. The tag is characterized by an amino acid sequence different from the amino acid sequence of any other detection tag encoded by the second nucleic acid library.
  ii. The tag is characterized by a molecular mass of between 200 and 5000 Da. In certain embodiments, the tag is characterized by a molecular mass of between 500 and 2500 Da. In certain embodiments, the tag is characterized by a molecular mass of between 900 and 2200 Da. In certain embodiments, the tag is characterized by a molecular mass of between 903 and 2180 Da.
  iii. The tag comprises a first severable element.

The mass specification given in ii relates to the mass of the tag after it has been isolated, i.e. after severing of the first severable element.

c. The polypeptide-encoding sequence comprised in the member of the first nucleic acid library is inserted into a member of said second nucleic acid library. Thereby, a tagged nucleic acid library encoding a tagged polypeptide library is created. Each member of the tagged polypeptide library comprises a polypeptide and a detection tag. The detection tag is separated from the polypeptide by the first severable element.

The tagged polypeptide library is a "nested library", because the polypeptide-encoding sequences of the first nucleic acid library are "nested" within members of the second nucleic acid library. The second nucleic acid library is several times larger than the tagged nucleic acid library. The tagged nucleic acid library is several times larger than the first nucleic acid library.

Within the tagged nucleic acid library, each polypeptide-encoding sequence of the first nucleic acid library is associated with a tag-encoding sequence of the second nucleic acid library. The association occurs in frame. The polypeptide-encoding sequence is inserted at a position where it will be subject to transcription and subsequent translation in a suitable host after the member of a tagged nucleic acid library is introduced into a suitable host. Introduction into bacterial cells can be accomplished by transformation. Introduction into non-bacterial cells can be accomplished by transfection. The skilled person is aware that a host is not necessarily required for translation: in vitro translation techniques may also be employed. For reviews on cell-free expression systems see Rosenblum, FEBS Lett. 2014 Jan. 21; 588(2):261-8 and Zemella, Chembiochem. 2015 November; 16(17):2420-31. The polypeptide-encoding sequence and the tag-encoding sequence will be transcribed within the same expressed sequence.

The tagged nucleic acid library comprises all polypeptide-encoding sequences of the first nucleic acid library, but only a subset of the tag-encoding sequences of the second nucleic acid library. Each member of the tagged nucleic acid library comprises only one polypeptide-encoding sequence and one tag-encoding sequence. Each tag encoding-sequence is comprised in only one member of the tagged nucleic acid library. In other words, each tag-encoding sequence is unique within the tagged nucleic acid library. Each polypeptide-encoding sequence may however be comprised in several members of the tagged nucleic acid library (redundant tagging). In certain embodiments, each polypeptide-encoding sequence of the first nucleic acid library is associated with at least one tag-encoding sequence of the second nucleic acid library. In certain embodiments, each polypeptide-encoding sequence of the first nucleic acid library is associated with at least two tag-encoding sequences of the second nucleic acid library. In certain embodiments, each polypeptide-encoding sequence of the first nucleic acid library is associated with at least five different tag-encoding sequences of the second nucleic acid library. In certain embodiments, each polypeptide-encoding sequence of the first nucleic acid library is associated with at least ten different tag-encoding sequences of the second nucleic acid library. In certain embodiments, each polypeptide-encoding sequence of the first nucleic acid library is associated on average with 10-30 different tag-encoding sequences of the second nucleic acid library. In certain embodiments, each polypeptide-encoding sequence of the first nucleic acid library is associated on average with approximately twenty different tag-encoding sequences of the second nucleic acid library.

d. A plurality of nucleic acid sequences is obtained from the tagged nucleic acid library. In particular, a nucleic acid sequence is obtained for every member of the tagged nucleic acid library. Each of said plurality of nucleic acid sequences comprises a polypeptide-encoding sequence and a tag-encoding sequence.

Based on the sequencing information obtained in step d, a database is created. The database comprises the sequences of all polypeptides and all detection tags comprised in the tagged polypeptide library. The skilled person is aware that the database may not comprise every single member of the tagged nucleic acid library, due to technical reasons. The sequences may be in the form of nucleic acid sequences and/or amino acid sequences. The database comprises the information which subset of the tag-encoding sequences of the second nucleic acid library is comprised in the tagged nucleic acid library. The database also comprises the information which tag-encoding sequence, or respectively, which tag-encoding sequences are associated with a given polypeptide-encoding sequence.

e. A mass spectrometry fragmentation pattern is predicted for each detection tag encoded by a tag-encoding sequence obtained in step d. The skilled person is aware that the fragmentation pattern is predicted for the isolated detection tag, that is for a detection tag that has been freed from its associated polypeptide by severing of the first severable element. The skilled person is aware that predicting the fragmentation pattern also comprises predicting the total mass of the isolated detection tag.

f. The tagged polypeptide library is expressed from the tagged nucleic acid library. As a consequence of the redundant tagging approach described in step c, the tagged polypeptide library may comprise a given member of said first polypeptide library tagged with several different detection tags (but only one tag per molecule). Redundant tagging is preferred, because it facilitates the unambiguous detection of a member of the first polypeptide library via multiple detection tags and minimizes potential influences of the detection tags on the biophysical properties of members of the tagged polypeptide library. The redundancy is in addition required for technical reasons: some detection tags may not be detected because they reduce expression levels, they are lost during sample preparation or they do not elute within the hydrophobicity window of the reversed phase column, which is analyzed by mass spectrometry.

g. A member of the tagged polypeptide library is selected in a selection step, yielding a selected polypeptide. This selection step comprises isolating those members of the tagged polypeptide library that fulfil defined biochemical criteria. In other words, a selection pressure is applied to the tagged polypeptide library. This selection pressure must lead to a physical separation of the proteins, so that physically separated sub-pools are generated and collected. A key advantage of the method according to the invention is that range of possible selection criteria is much higher than in protein display methods. By way of non-limiting example, the criteria may be selected from the group of criteria comprising the ability to bind to a target molecule with a defined affinity, stability of a polypeptide at defined conditions, a certain aggregation behaviour (e.g. predominant occurrence as a monomer) at defined conditions, resistance towards proteases, tissue penetration abilities, fast or slow clearance from the blood stream, the ability to penetrate the blood-brain-barrier, and the ability to accumulate in tumors.

h. The first severable element is severed. Thereby, the detection tag is separated from the selected polypeptide and an isolated detection tag is yielded.

i. The isolated detection tag is identified and quantified in the following way:
  i. The fragmentation pattern of the isolated detection tag is recorded by mass spectrometry. The fragmentation pattern provides information about mass and hydrophobicity of fragments of the isolated detection tag. The fragmentation pattern yields information about the amino acid sequence of the isolated detection tag.
  ii. The mass and fragmentation pattern obtained in step i is matched with the mass and fragmentation patterns predicted in step e. Thereby, the isolated detection tag is identified. The combination of the information obtained by mass spectrometry with the information obtained by sequencing of the tagged nucleic acid library allows the unambiguous identification of a given detection tag.

The matching precision of predicted and recorded fragmentation patterns can be scored and allows ranking of polypeptide library members. Comparison of polypeptide rankings between different selection conditions can be used as a relative measure of various characteristics of polypeptides (e.g. off-rate, tissue distribution, conformation-specific binding, etc.). The comparison is most accurate for redundantly tagged polypeptide library members, where differences in fragmentation pattern recording efficiencies of individual tags are averaged out.

The score of the matching precision of predicted and recorded fragmentation patterns can be used as a measure of relative quantities of polypeptide library members after selection. The relative quantities are most accurate for redundantly tagged polypeptide library members, where differences in fragmentation pattern recording efficiencies of individual tags are averaged out.

j. The nucleic acid sequence comprising the tag-encoding sequence encoding the detection tag identified in step i is selected from the plurality of nucleic acid sequences obtained in step d. Thereby, the member of the tagged polypeptide library associated with the detection tag identified in step i is identified.

The skilled person is aware that steps g to j are performed for a number of different members of said tagged polypeptide library in parallel. A pool of several polypeptides displaying the defined criteria is selected in step g, and all of these polypeptides are identified via mass spectrometry analysis of their detection tags. The skilled person is aware that due to technical reasons, not every single polypeptide may be identified in this step.

The mass spectrometry analysis performed in step i is quantitative, thus the method according to the invention allows not only to identify a polypeptide but also to quantify the amount of this polypeptide in a sample.

To ensure redundant and unique tagging, it is important that
  i) the first library has a limited, defined size. In certain embodiments, the first nucleic acid library has a size of 5 to 100.000. In certain embodiments, the first nucleic acid library has a size of 100 to 50.000. In certain embodiments, the first nucleic acid library has a size of 500 to 5.000.
  ii) the second nucleic acid library has a size of $10^3$ to $10^{11}$, particularly $10^5$ to $10^{10}$, more particularly $10^6$ to $10^9$, even more particularly approximately $10^8$ before the insertion step of the first library
  iii) after the insertion step, the chosen subset of the plurality of polypeptide/tag combination plasmids is at least 3×, particularly at least 5×, more particularly at least 15×, even more particularly at least 25× the number of members of said first nucleic acid library.
  iv) the chosen subset of the plurality of polypeptide/tag combination plasmids is less than 50%, particularly less than 5%, more particularly less than 0.5%, even more particularly less than 0.05% of the number of members of said second nucleic acid library.

The size of the library can be controlled by a diversity restriction step prior to step a, in which the first library is selected as a subset from a larger pre-library.

The method according to the invention allows the analysis of protein libraries in the absence of the physical genotype-phenotype linkage required for protein display methods. This eliminates the disadvantage of having large physical entities (e.g. a phage or a ribosome and the encoding DNA or RNA) attached to the members of the protein library. Entire protein libraries can be screened as a pool for criteria of choice, instead of testing individual proteins as it is usually the case for protein screens. However, even though entire protein pools are processed, the readout is similarly to screens as every single protein is characterized individually. This is of particular relevance in the field of the development of binding proteins (drugs, diagnostics, research tools etc.). A range of protein characteristics can be analyzed in thousands of candidates at once. An exemplary question would be: Which binder candidates are stable, soluble and monomeric?

The method according to the invention allows addressing the relevant question right at the beginning of the protein therapeutic development chain: "Which binder has the largest therapeutic potential in vivo?" Questions regarding the therapeutic potential are: Which binder survives the harsh condition in the gut upon oral administration? Which binder crosses the blood-brain-barrier? Which binder displays the optimal renal clearance property from the blood? Which binder, among thousands, displays a good tissue penetration at the relevant tissue?

In certain embodiments, the detection tag is characterized by a hydrophobicity value of between −27 and 128. In certain embodiments, the detection tag is characterized by a hydrophobicity value of between −1 and 70. The hydrophobicity value relates to the mass of the detection tag after it has been isolated, i.e. after severing of the first severable element. The hydrophobicity value does not include the associated affinity tag.

In certain embodiments, the member of the tagged polypeptide library is associated with an affinity tag. Such affinity tag may simplify purification of the selected member of the tagged polypeptide library and/or of the detection tag itself prior to mass spectrometry. The affinity tag and the member of the tagged polypeptide library are comprised within one primary amino acid sequence. Each member of the tagged polypeptide library comprises a polypeptide and a detection tag. The affinity tag may be associated with either the polypeptide or with the detection tag.

In certain embodiments, the affinity tag is selected from the group comprising a His-tag, a CBP-tag, a CYD-tag, a Strep-tag, a StrepII-tag, a FLAG-tag, a HPC-tag, a GST-tag, an Avi-tag, a biotinylation tag, a Myc-tag, a 3×FLAG tag and a MBP-tag.

In certain embodiments, the detection tag is associated with an affinity tag. In these instances, the affinity tag is located at the C-terminus of the detection tag. This arrangement has the further advantage that the detection tag is protected from degradation by peptidases and it ensures that only non-degraded polypeptides associated with complete detection tags are isolated during protein purification. The skilled person is aware that the expression "affinity tag is located at C-terminus of detection tag" does not necessarily imply that the affinity tag is located immediately C-terminal of the detection tag, but that there may be a linker of several amino acids separating the affinity tag and the detection tag.

In certain embodiments, the affinity tag is separated from said detection tag by a second severable element, and said second severable element is severed prior to step i. Thus, only the detection tag without the associated affinity tag is analysed by mass spectrometry.

The mass and fragmentation pattern specifications of the detection tag relate to the mass and fragmentation pattern of the tag after it has been separated from the associated polypeptide and the affinity tag, i.e. after severing of the first and second severable elements. The skilled person is aware that in instances where the detection tag is not freed from an associated affinity tag prior to mass spectrometry, this will influence the results of the mass spectrometry analysis. If all detection tags are associated with the same affinity tag, the changes in mass and fragmentation pattern can be accounted for, therefore it will still be possible to identify the detection tag, although not as efficient and clear-cut as in instances where the detection tag has been separated from the affinity tag by severing of the second severable element.

In certain embodiments, the affinity tag is a His-tag.

In certain embodiments, step h comprises analysing the isolated detection tag via liquid chromatography coupled to electrospray ionization mass spectrometry (LC-MS). In certain embodiments, this step comprises liquid reverse-phase chromatography. The isolated detection tags are separated according to their hydrophobicity by reversed phase chromatography to reduce sample complexity. Subsequently, their mass and peptide fragmentation pattern is recorded by mass spectrometry.

In certain embodiments, step d comprises sequencing of the complete tagged expression library with a coverage of ≤5×. In certain embodiments, step d comprises deep sequencing of the tagged expression library.

In certain embodiments, step d comprises inserting the polypeptide-encoding sequence and the tag-encoding sequence comprised in the tagged nucleic acid library together into a sequencing vector. Deep sequencing usually comprises a PCR amplification step. The inventors noticed that PCR amplification leads to a significant number of recombination events between gene segments of the tagged library members. Thus, they constructed a set of deep sequencing plasmids, which permit the attachment of sequence elements required for deep sequencing by restriction digest and ligation, thereby eliminating the need for PCR amplification of the nested library prior to deep sequencing.

In certain embodiments, the isolated detection tag consists of 5 to 30 contiguous amino acids and comprises one and only one amino acid having a positively charged side chain. In certain embodiments, the isolated detection tag consists of 7 to 21 contiguous amino acids and comprises one and only one amino acid having a positively charged side chain.

In certain embodiments, the isolated detection tag consists of 11 to 15 contiguous amino acids and comprises one and only one amino acid having a positively charged side chain.

In certain embodiments, the amino acid having a positively charged side chain is located at the C-terminus of the isolated detection tag. In certain embodiments, the amino acid having a positively charged side chain is selected from arginine (R) and lysine (K). In certain embodiments, the amino acid having a positively charged side chain is an arginine (R) located at the C-terminus of the isolated detection tag.

The skilled person is aware that in addition to the amino acid having a positively charged side chain, the isolated detection tag carries another positive charge at neutral pH, which is the primary amine at the N terminus of the isolated detection tag.

In certain embodiments, the isolated detection tag comprises a sequence element I selected from a collection of sequence elements I, wherein said sequence element I consists of 5 to 10, particularly 7 amino acids, independently of each other selected from A, S, T, N, Q, D, E, V, L, I, F, Y, W, G and P.

In certain embodiments, the one and only one amino acid having a positively charged side chain is located at the C-terminus of the isolated detection tag and the remaining amino acids are independently selected from A, S, T, N, Q, D, E, V, L, I, F, Y, W, G and P. In certain embodiments, the one and only one amino acid having a positively charged side chain is a R located at the C-terminus of the isolated detection tag.

The isolated detection tags are optimally detectable by mass spectrometry, in particular by LC-MS (liquid reverse-phase chromatography coupled to ESI-MS). Amino acids C and M were omitted in the design of the detection tag because they are prone to oxidation. Amino acids K, R and H were omitted in the sequence element I, because they would add an additional amino acid with a positively charged side chain to the tag, which was not desired because the tag would carry an additional charge during ESI-MS detection and fall outside of the optimal detection range. K and R would add additional trypsin cleavage sites into the tag sequence, which was not desired.

Adding a K to the amino acid sequence of the detection tag would add another primary amine, which would complicate labelling of the detection tag by isobaric tags for relative and absolute quantitation by mass spectrometry using NHS chemistry.

In certain embodiments, the isolated detection tag comprises
  a. sequence element I, wherein sequence element I consists of 5 to 10, particularly 7 contiguous amino acids, independently of each other selected from A, S, T, N, Q, D, E, V, L, I, F, Y, W, G and P; and
  b. sequence element II selected from SEQ ID NO 01 (WR), SEQ ID NO 02 (WLR), SEQ ID NO 03 (WQSR), SEQ ID NO 04 (WLTVR) and SEQ ID NO 05 (WQEGGR).

In certain embodiments, the isolated detection tag consists of
  a. sequence element III: GS;
  b. sequence element I, wherein sequence element I consists of 5 to 10, particularly 7 contiguous amino acids, independently of each other selected from A, S, T, N, Q, D, E, V, L, I, F, Y, W, G and P; and c. sequence element II selected from SEQ ID NO 01 (WR), SEQ ID NO 02 (WLR), SEQ ID NO 03 (WQSR), SEQ ID NO 04 (WLTVR) and SEQ ID NO 05 (WQEGGR).

The order of the sequence elements from N-terminus to C-terminus is: sequence element III, sequence element I, sequence element II. These detection tags fall within a mass range between 903 and 2180 Da, which is optimal for sensitive detection by ESI-MS. The isolated tags carry two positive charges at physiological pH and below, namely an R at the C-terminus and the N-terminal primary amine. The positive charge at the C-terminus of the isolated detection tag facilitates ionization of the tag for mass spectrometry detection and acts as unique trypsin cleavage site. Peptides with C-terminal arginines or lysines are particularly well detectable by mass spectrometry (favorable ionization properties). In each isolated detection tag the N-terminal amine is the only primary amine, which is used for amine coupling through NHS chemistry. This permits to attach labels for quantitative mass spectrometry to perform for example iTRAQ (isobaric tags for relative and absolute quantification). The detection tags were engineered to display a range of hydrophobicities ideally suited for peptide separation by standard reversed-phase chromatography columns.

In certain embodiments, all sequence elements I comprised in the first nucleic acid library together constitute a collection of sequence elements I. Within the collection of sequence elements I, each amino acid occurs with a frequency specified in table 1.

TABLE 1

| A | S | T | N | Q | D | E | V | L | F | Y | W | G | P | Total |
|---|---|---|---|---|---|---|---|---|---|---|---|---|---|---|
| 18 | 6 | 12 | 1 | 1 | 11 | 11 | 12 | 2 | 1 | 4 | 1 | 8 | 12 | 100 |

In certain embodiments, one of said first and/or said second severable element is or comprises a protease recognition sequence. In certain embodiments, both said first and said second severable elements are or comprise a protease recognition sequence.

In certain embodiments, the first severable element is or comprises a thrombin recognition sequence and/or the second severable element is or comprises a trypsin recognition sequence.

Collection of Polypeptides

According to a second aspect, a collection of polypeptides is provided. Each member of the collection of polypeptides is associated with a detection tag. In certain embodiments, each member of the collection of polypeptides is associated with at least one detection tag. The expression "associated with at least one detection tag" refers to the fact that each member of the collection of polypeptides can be associated with more than one detection tag, but only one tag per polypeptide molecule. In other words, the collection of polypeptides may comprise a polypeptide A associated with detection tag X and a polypeptide A associated with detection tag Y, but not a polypeptide A associated with both detection tags X and Y. In certain embodiments, each member of the collection of polypeptides is associated with at least two detection tags. In certain embodiments, each member of the collection of polypeptides is associated with at least five detection tags. In certain embodiments, each member of the collection of polypeptides is associated with at least ten detection tags. In certain embodiments, each member of the collection of polypeptides is associated with approximately twenty detection tags. Each detection tag has the following characteristics:
  a. The tag is characterized by an amino acid tag sequence different from the amino acid sequence of any other detection tag encoded by the plurality of expression vectors.
  b. The tag is characterized by a molecular mass of between 200 and 5000 Da. In certain embodiments, the tag is characterized by a molecular mass of between 500 and 2500 Da. In certain embodiments, the tag is characterized by a molecular mass of between approximately 900 and approximately 2200 Da. In certain embodiments, the tag is characterized by a molecular mass of between 903 and 2180 Da.
  c. The tag is separated from said member of said collection of polypeptides by a first severable element.

In certain embodiments of the second aspect of the invention, the detection tag is characterized by a hydrophobicity value of between −27 and 128. In certain embodiments, the detection tag is characterized by a hydrophobicity value of between −1 and 70.

In certain embodiments of the second aspect of the invention, the member of the collection of polypeptides is associated with an affinity tag.

In certain embodiments of the second aspect of the invention, the detection tag is associated with an affinity tag. The affinity tag and the detection tag are comprised within the same primary amino acid sequence. The affinity tag is separated from the detection tag by a second severable element. The detection tag can be freed from the affinity tag via severing of the second severable element. In certain embodiments, the affinity tag is selected from the group comprising a His-tag, a CBP-tag, a CYD-tag, a Strep-tag, a StrepII-tag, a FLAG-tag, a HPC-tag, a GST-tag, an Avi-tag, a biotinylation tag, a Myc-tag, a 3×FLAG tag and a MBP-tag. In certain embodiments, the affinity tag is a His-tag.

In certain embodiments of the second aspect of the invention, the isolated detection tag consists of 5 to 30 contiguous amino acids and comprises one and only one amino acid having a positively charged side chain. In certain embodiments, the isolated detection tag consists of 7 to 21 contiguous amino acids and comprises one and only one amino acid having a positively charged side chain. In certain embodiments, the isolated detection tag consists of 11 to 15 contiguous amino acids and comprises one and only one amino acid having a positively charged side chain.

In certain embodiments, the amino acid having a positively charged side chain is located at the C-terminus of the isolated detection tag. In certain embodiments, the amino acid having a positively charged side chain is selected from arginine (R) and lysine (K). In certain embodiments, the amino acid having a positively charged side chain is an arginine (R) located at the C-terminus of the isolated detection tag.

In certain embodiments of the second aspect of the invention, the detection tag comprises
  a. sequence element I, wherein sequence element I consists of 5 to 10, particularly 7 contiguous amino acids, independently of each other selected from A, S, T, N, Q, D, E, V, L, I, F, Y, W, G and P; and
  b. sequence element II selected from SEQ ID NO 01 (WR), SEQ ID NO 02 (WLR), SEQ ID NO 03 (WQSR), SEQ ID NO 04 (WLTVR) and SEQ ID NO 05 (WQEGGR).

Detection Tag

According to a third aspect, a peptide detection tag is provided, which is designed for optimal detection by mass spectrometry. The detection tag consists of 4 to 20 amino acids and has the following features:
a. The detection tag comprises only one amino acid having a positively charged side chain.
b. The detection tag is characterized by a molecular mass of between 200 and 5000 Da. In certain embodiments, the detection tag is characterized by a molecular mass of between 500 and 2500 Da. In certain embodiments, the detection tag is characterized by a molecular mass of between 900 and 2200 Da. In certain embodiments, the tag is characterized by a molecular mass of between 903 and 2180 Da.

In certain embodiments of the third aspect of the invention, the detection tag consists of 7 to 18 amino acids. In certain embodiments of the third aspect of the invention, the detection tag consists of 11 to 15 amino acids.

In certain embodiments of the third aspect of the invention, the detection tag essentially consists of
a. a sequence element I, wherein said sequence element I consists of 5 to 10, particularly 7 contiguous amino acids, independently of each other selected from A, S, T, N, Q, D, E, V, L, I, F, Y, W, G and P; and
b. a sequence element II selected from SEQ ID NO 01 (WR), SEQ ID NO 02 (WLR), SEQ ID NO 03 (WQSR), SEQ ID NO 04 (WLTVR) and SEQ ID NO 05 (WQEGGR).

Collection of Detection Tags

According to another aspect, a collection of peptide tags is provided. The collection of peptide tags comprises the peptide tags according to the third aspect of the invention. Each detection tag comprised in the collection of peptide tags consists of 4 to 20 amino acids and is characterized by an amino acid sequence different from the amino acid sequence of any other detection tag comprised in said collection of detection tags. In certain embodiments, each detection tag consists of 7 to 18 amino acids. In certain embodiments, each detection tag consists of 11 to 15 amino acids. In certain embodiments, the collection of peptide tags comprises at least 96 peptide tags. In certain embodiments, the collection of peptide tags comprises at least 500.000 peptide tags. In certain embodiments, the collection of peptide tags comprises at least $10^7$ peptide tags. In certain embodiments, the collection of peptide tags comprises approximately $10^8$ peptide tags.

In certain embodiments of this aspect of the invention, the detection tag comprises only one amino acid having a positively charged side chain and the remaining amino acids are selected from A, S, T, N, Q, D, E, V, L, I, F, Y, W, G and P.

In certain embodiments of this aspect of the invention, the tag is characterized by a hydrophobicity value of between between −27 and 128. In certain embodiments, the detection tag is characterized by a hydrophobicity value between −1 and 70.

In certain embodiments of this aspect of the invention, the detection tag is associated with an affinity tag. In certain embodiments, the affinity tag is selected from the group comprising a His-tag, a CBP-tag, a CYD-tag, a Strep-tag, a StrepII-tag, a FLAG-tag, a HPC-tag, a GST-tag, an Avi-tag, a biotinylation tag, a Myc-tag, a 3×FLAG tag and a MBP-tag. In certain embodiments the affinity tag is a His-tag. The affinity tag and the detection tag are comprised within the same primary amino acid sequence. The affinity tag is separated from the detection tag by a severable element.

In certain embodiments of this aspect of the invention, the detection tag essentially consists of
a. a sequence element I, wherein said sequence element I consists of 5 to 10, particularly 7 contiguous amino acids, independently of each other selected from A, S, T, N, Q, D, E, V, L, I, F, Y, W, G and P; and
b. a sequence element II selected from SEQ ID NO 01 (WR), SEQ ID NO 02 (WLR), SEQ ID NO 03 (WQSR), SEQ ID NO 04 (WLTVR) and SEQ ID NO 05 (WQEGGR).

Collection of Plasmid Vectors

According to yet another aspect, a collection of plasmid vectors is provided. Each member of said collection of plasmid vectors comprises a nucleic acid sequence encoding a detection tag. Each detection tag consists of 4 to 20 amino acids and is characterized by an amino acid sequence different from the amino acid sequence of any other detection tag encoded by said collection of plasmid vectors. In certain embodiments, each detection tag consists of 7 to 18 amino acids. In certain embodiments, each detection tag consists of 11 to 15 amino acids. In certain embodiments, the collection of plasmid vectors comprises at least 96 plasmid vectors. In certain embodiments, the collection of plasmid vectors comprises at least 500,000 plasmid vectors. In certain embodiments, the collection of plasmid vectors comprises at least $10^7$ plasmid vectors. In certain embodiments, the collection of plasmid vectors comprises approximately $10^8$ plasmid vectors.

In certain embodiments of this aspect of the invention, the detection tag comprises only one amino acid having a positively charged side chain.

In certain embodiments of this aspect of the invention, the detection tag is characterized by a molecular mass of between 200 and 5000 Da. In certain embodiments, the detection tag is characterized by a molecular mass of between 500 and 2500 Da. In certain embodiments, the detection tag is characterized by a molecular mass of between 900 and 2200 Da. In certain embodiments, the detection tag is characterized by a molecular mass of between 903 and 2180 Da.

In certain embodiments of this aspect of the invention, the tag is characterized by a hydrophobicity value of between between −27 and 128. In certain embodiments, the detection tag is characterized by a hydrophobicity value between −1 and 70.

In certain embodiments of this aspect of the invention, the detection tag is associated with an affinity tag. In certain embodiments, the affinity tag is selected from the group comprising a His-tag, a CBP-tag, a CYD-tag, a Strep-tag, a StrepII-tag, a FLAG-tag, a HPC-tag, a GST-tag, an Avi-tag, a biotinylation tag, a Myc-tag, a 3×FLAG tag and a MBP-tag. In certain embodiments the affinity tag is a His-tag. The affinity tag and the detection tag are comprised within the same primary amino acid sequence. The affinity tag is separated from the detection tag by a second severable element.

In certain embodiments of this aspect of the invention, the detection tag essentially consists of
a. a sequence element I, wherein said sequence element I consists of 5 to 10, particularly 7 contiguous amino acids, independently of each other selected from A, S, T, N, Q, D, E, V, L, I, F, Y, W, G and P; and
b. a sequence element II selected from SEQ ID NO 01 (WR), SEQ ID NO 02 (WLR), SEQ ID NO 03 (WQSR), SEQ ID NO 04 (WLTVR) and SEQ ID NO 05 (WQEGGR).

In certain embodiments of this aspect of the invention, each member of the collection of plasmid vectors comprises
a. a negative selection cassette flanked 5' with a first endonuclease restriction site and 3' with a second endonuclease restriction site;
b. a promotor located 5' of the first endonuclease restriction site;
c. the nucleic acid tag sequence encoding the detection tag, located 3' of the second endonuclease restriction site. In certain embodiments, the nucleic acid sequence encoding the detection tag and the second endonuclease restriction site are separated by less than 100 base pairs. In certain embodiments, the nucleic acid sequence encoding the detection tag and the second endonuclease restriction site are separated by less than 50 base pairs. In certain embodiments, the nucleic acid sequence encoding the detection tag and the second endonuclease restriction site are separated by approximately 20 base pairs. In certain embodiments, the base pairs located between the nucleic acid sequence encoding the detection tag and the second endonuclease restriction site encode a first severable element.

In certain embodiments of this aspect of the invention, each member of the collection of plasmid vectors comprises
a. the nucleic acid tag sequence encoding the detection tag, associated within the same reading frame with a nucleic acid sequence encoding a polypeptide;
b. a diversity element comprising non-identical bases to prevent signal overload during sequencing;
c. a primer binding site for binding of sequencing primers;
d. an index element comprising one of several defined nucleic acid sequences for multiplexing;
e. an adapter element to immobilize the DNA molecule during sequencing and
f. two endonuclease restriction sites flanking elements a-e to release the DNA fragment from the plasmid vector prior to sequencing.

The plasmid vectors described in the previous embodiment serve as deep sequencing plasmids. Preferentially, these vectors do not comprise the affinity tag in order to reduce the length of the fragment to be sequenced.

Method of Protein Detection

According to another aspect, a method of protein detection is provided. The method comprises the following steps:
a. A nucleic acid library encoding a polypeptide library is provided. Each polypeptide comprised in the polypeptide library is associated with a detection tag. Polypeptide and detection tag are comprised within the same primary amino acid sequence. Each detection tag has the following characteristics:
  i. The tag is characterized by an amino acid sequence different from the amino acid sequence of any other detection tag encoded by the nucleic acid library.
  ii. The tag is characterized by a molecular mass of between 200 and 5000 Da. In certain embodiments, the tag is characterized by a molecular mass of between 500 and 2500 Da. In certain embodiments, the tag is characterized by a molecular mass of between approximately 900 and approximately 2200 Da. In certain embodiments, the tag is characterized by a molecular mass of between 903 and 2180 Da.
  iii. The tag is separated from the associated polypeptide by a first severable element.

Each detection tag encoded by the nucleic acid library is unique with respect to any other detection tag encoded by the nucleic acid library. Each polypeptide comprised in the polypeptide library is associated with at least one detection tag. In certain embodiments, each polypeptide comprised in the polypeptide library is associated with at least two detection tags. In certain embodiments, each polypeptide comprised in the polypeptide library is associated with at least five detection tags. In certain embodiments, each polypeptide comprised in the polypeptide library is associated with at least ten detection tags. In certain embodiments, each polypeptide comprised in the polypeptide library is associated with approximately twenty detection tags. Each polypeptide molecule comprises only one detection tag.

b. A database is provided. The database comprises the following information:
  i. A plurality of nucleic acid and/or amino acid sequences. The plurality of sequences comprises the sequences of all members of the nucleic acid library. Each of the sequences comprises a sequence specifying a polypeptide and a sequence specifying a detection tag.
  ii. A mass spectrometry fragmentation pattern for each detection tag encoded by the nucleic acid library.
c. The polypeptide library is expressed from the nucleic acid library.
d. A member of the polypeptide library is selected in a selection step, yielding a selected polypeptide.
e. The first severable element is severed. Thereby, the detection tag is separated from the selected polypeptide and an isolated detection tag is yielded.
f. The isolated detection tag is identified in the following way:
  i. The fragmentation pattern of the isolated detection tag is recorded by mass spectrometry.
  ii. The fragmentation pattern obtained in step i is matched with the predicted fragmentation pattern in the provided database. Thereby, the isolated detection tag is identified. The combination of the information obtained by mass spectrometry with the information obtained by sequencing of the tagged nucleic acid library allows the unambiguous identification of a given detection tag.
g. The sequence specifying the detection tag identified in step f is selected from the plurality of sequences comprised in the database. Thereby, the member of the polypeptide library associated with the detection tag identified in step f is identified.

In certain embodiments, each member of said polypeptide library is associated with an affinity tag.

In certain embodiments, each detection tag is associated with an affinity tag.

In certain embodiments, the affinity tag is selected from the group comprising a His-tag, a CBP-tag, a CYD-tag, a Strep-tag, a StrepII-tag, a FLAG-tag, a HPC-tag, a GST-tag, an Avi-tag, a biotinylation tag, a Myc-tag, a 3×FLAG tag and a MBP-tag.

In certain embodiments, the affinity tag is separated from said detection tag by a second severable element, and said second severable element is severed prior to step f. Thus, only the detection tag without the associated affinity tag is analysed by mass spectrometry.

The mass and fragmentation pattern specifications of the detection tag relate to the mass and fragmentation pattern of the tag after it has been separated from the associated polypeptide and the affinity tag, i.e. after severing of the first and second severable elements. The skilled person is aware that in instances where the detection tag is not freed from an associated affinity tag prior to mass spectrometry, this will influence the results of the mass spectrometry analysis. As all detection tags are associated with the same affinity tag, the changes in mass and fragmentation pattern can be accounted for, therefore it will still be possible to identify the detection tag, although not as efficient and clear-cut as in instances where the detection tag has been separated from the affinity tag by severing of the second severable element.

In certain embodiments, the affinity tag is a His-tag.

The skilled person is aware that steps d to g are performed for a number of different members of the polypeptide library in parallel. A pool of several polypeptides is selected in step g, and all of these polypeptides are identified via mass spectrometry analysis of their detection tags. The skilled person is aware that due to technical reasons, not every single polypeptide may be identified in this step.

The mass spectrometry analysis performed in step f is quantitative, thus the method according to the invention allows not only to identify a polypeptide but also to quantify the amount of this polypeptide in a sample.

Method of Associating a Polypeptide with a Unique Detection Tag

According to yet another aspect, a method of associating a polypeptide with a unique detection tag is provided. The method comprises the following steps:
   a. A first nucleic acid library is provided. Each member of the first nucleic acid library comprises a polypeptide-encoding sequence encoding a member of a first polypeptide library;
   b. A second nucleic acid library is provided. Each member of the second nucleic acid library comprises a tag-encoding sequence encoding a detection tag. Each detection tag has the following characteristics:
      i. The tag is characterized by an amino acid sequence different from the amino acid sequence of any other detection tag encoded by the second nucleic acid library;
      ii. The tag is characterized by a molecular mass of between 200 and 5000 Da. In certain embodiments, the tag is characterized by a molecular mass of between 500 and 2500 Da. In certain embodiments, the tag is characterized by a molecular mass of between approximately 900 and approximately 2200 Da. In certain embodiments, the tag is characterized by a molecular mass of between 903 and 2180 Da.
   c. The polypeptide-encoding sequence comprised in the member of the first nucleic acid library is inserted into a member of the second nucleic acid library. Thereby, a plurality of polypeptide-tag combination plasmids is generated.
   The first nucleic acid library has a size of 5 to 100.000. In certain embodiments, the first nucleic acid library has a size of 100 to 50.000. In certain embodiments, the first nucleic acid library has a size of 500 to 5.000.
   The second nucleic acid library has a size of $10^3$ to $10^{11}$. In certain embodiments, the second nucleic acid library has a size of $10^5$ to $10^{10}$. In certain embodiments, the second nucleic acid library has a size of $10^6$ to $10^9$. In certain embodiments, the second nucleic acid library has a size of approximately $10^8$.
   Within the plurality of polypeptide/tag combination plasmids, each polypeptide-encoding sequence of the first nucleic acid library is associated with a tag-encoding sequence of the second nucleic acid library. The association occurs within the same reading frame.
   d. A subset of the plurality of polypeptide-tag combination plasmids is selected. This selection step comprises selecting a defined number of clones, wherein each clone comprises one member of the plurality of polypeptide-tag combination plasmids. Thereby, a tagged nucleic acid library encoding a tagged polypeptide library is generated. Each member of the tagged polypeptide library comprises a polypeptide and a detection tag. Each tag is comprised in only one member of the tagged polypeptide library. In other words, each detection tag is unique within the tagged polypeptide library. Each polypeptide may however be comprised in several members of the tagged polypeptide library (redundant tagging).
   In certain embodiments, each polypeptide is associated with at least one detection tag. In certain embodiments, each polypeptide is associated with at least two detection tags. In certain embodiments, each polypeptide is associated with at least five detection tags. In certain embodiments, each polypeptide is associated with at least ten detection tags. In certain embodiments, each polypeptide is associated with approximately twenty detection tags.

In certain embodiments of this aspect of the invention, the selected subset of the plurality of polypeptide-tag combination plasmids is at least 10× the number of members of the first nucleic acid library. In certain embodiments, the selected subset of the plurality of polypeptide-tag combination plasmids is at least 20× the number of members of the first nucleic acid library.

In certain embodiments of this aspect of the invention, the selected subset of the plurality of polypeptide-tag combination plasmids is less than 50% of the number of members of the second nucleic acid library. In certain embodiments of this aspect of the invention, the selected subset of the plurality of polypeptide-tag combination plasmids is less than 5% of the number of members of the second nucleic acid library. In certain embodiments of this aspect of the invention, the selected subset of the plurality of polypeptide-tag combination plasmids is less than 0.05% of the number of members of the second nucleic acid library.

By choosing the optimal size of the selected subset of the plurality of polypeptide-tag combination plasmids, it is ensured that in the tagged polypeptide library, each detection tag is unique (present only once), but each polypeptide is present several times, each time associated with a different detection tag.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

EXAMPLES

The Flycode Sequence Library

A randomized library of short DNA-encoded peptides was designed to be optimally detectable by mass spectrometry (MS), in particular by LC-MS (liquid reverse-phase chromatography coupled to ESI-MS). The peptides fall within a mass range between 903 and 2180 Da, which is optimal for sensitive detection by ESI-MS. Flycodes carry two positive charges at physiological pH and below, namely an R at the C-terminus and the N-terminal primary amine. The positive charge at the C-terminus of the flycode facilitates ionization of the peptide for mass spectrometry detection and acts as unique trypsin cleavage site. In each flycode the N-terminal amine is the only primary amine, which is used for amine coupling through simple NHS chemistry. This permits to attach labels for quantitative mass spectrometry to perform for example iTRAQ (isobaric tags for relative and absolute quantification). The flycodes were engineered to display a range of hydrophobicities ideally suited for peptide separation by standard reversed-phase chromatography columns.

The flycode library consists of two parts plus flanking amino acids that are constant, namely GS at the N-terminus and R at the C-terminus. The N-terminal "GS" sequence is part of the thrombin protease cleavage site, which remains at the flycode after cleavage.

Part 1: The barcode region encompasses 7 consecutive randomized amino acid positions. The average frequency of amino acids is given in the table 1 above (in %).

Not all twenty natural amino acids are present in the barcode (C, M, K, R, H and I are missing). C and M were omitted because they are prone to oxidation. K, R and H were omitted because they would add an additional positive charge to the flycode sequence, which was not desired because the peptide would in such a case carry an additional charge during ESI-MS detection and fall outside of the optimal detection range. K and R would add additional trypsin cleavage sites into the flycode sequence, which was not desired. K would add another primary amine, which would complicate peptide labelling by NHS chemistry. Isoleucine was omitted because it cannot be distinguished by mass from Leucine.

Part 2: The C-terminus was constructed in 5 different variants, which are equally frequent in the flycode library and which all end with an R. They are as well devoid of C, M, K, H and I. The flycodes consist therefore minimally of 11 amino acids and maximally of 15 amino acids (GS+7 randomized residues+2-6 C-terminal residues). The 5 different C-terminal endings are listed here:

SEQ ID NO 01 (WR), SEQ ID NO 02 (WLR), SEQ ID NO 03 (WQSR), SEQ ID NO 04 (WLTVR), SEQ ID NO 05 (WQEGGR).

The NestLink Expression Vector pLNx Containing the Flycode Library.

Figure 2:
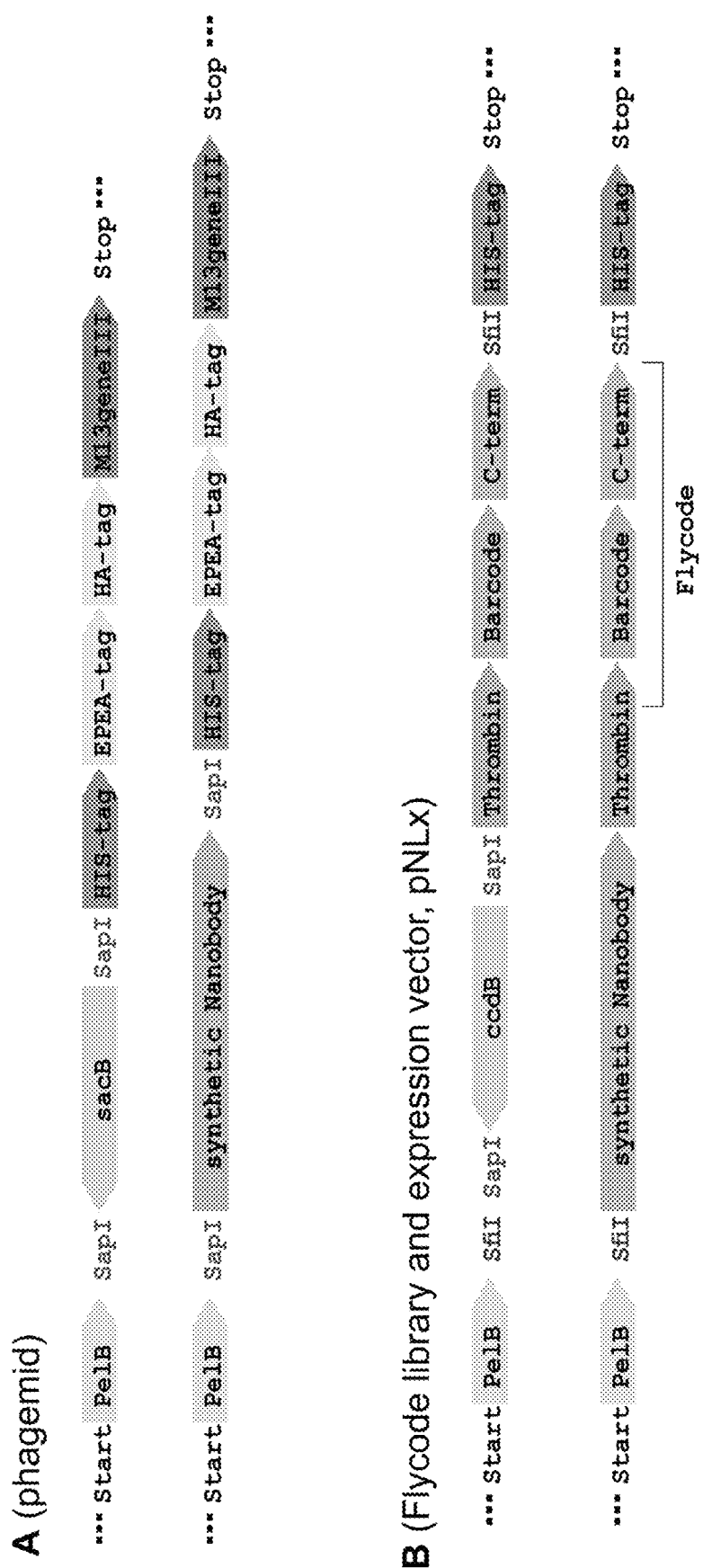
FIG. 2 shows the relevant plasmid designs for the NestLink technology before (upper strings) and after library insertion (lower strings). A) The phagemid used for phage display selections of nanobodies against target molecules. The phagemid carries two SapI restriction sites that allow insertion of nanobody libraries and their efficient transfer to the NestLink expression vector pNLx after enrichment by phage display. B) the NestLink expression vector pNLx harboring the Flycode diversity of approximately $10^8$ variants. The SapI sites are designed to vanish upon nanobody library insertion. The flycoded nanobodies can be specifically excised from the expression vector via SfiI restriction. The placement of the Sfi-sites ensures deepsequencing of the entire nanobodies attached to their corresponding Flycodes, but minimizes the deepsequencing read length by exclusion of redundant sequences, such as PelB and the His-tag. C) A set of deepsequencing vectors (pLNs) with various indices were generated each harboring all necessary sequences for Illumine MiSeq sequencing. The flycoded nanobodies are inserted into this vector via Sfi restriction and ligation. Subsequently, they are released as a linear fragment containing all MiSeq adapter regions by BseRI restriction. In this manner, no PCR is required to generate DNA fragments for MiSeq analysis, which would result in recombination events in the nanobody-Flycode sequences and thereby destroy the linkage between Flycode and nanobody sequence. D) Deepsequencing adaptors can also be attached via synthetic double-stranded adaptor oligonucleotides via appropriate single-strand overhangs complementary to the SfiI restriction site encoded in pNLx.
Figure 2:
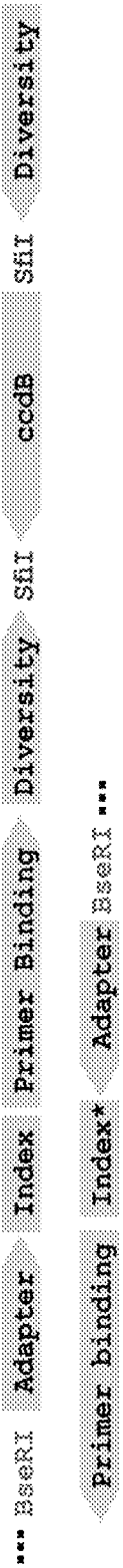
Figure 2:
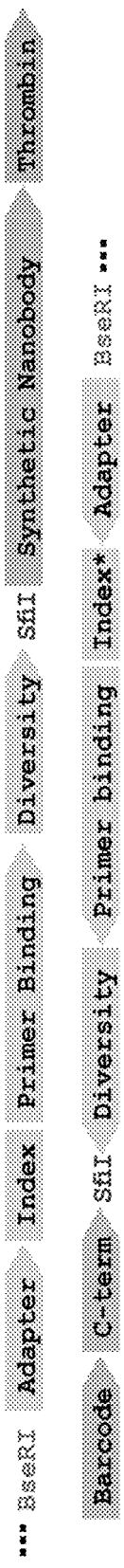
Figure 2:
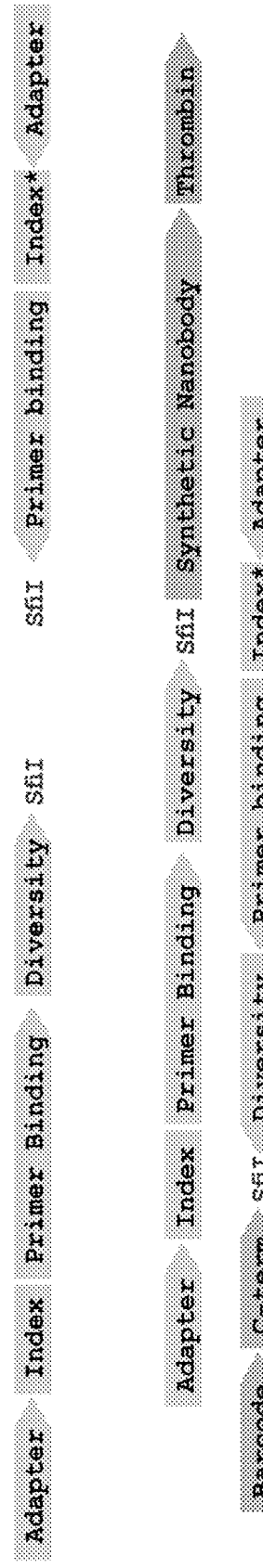
Figure 2:

The NestLink expression vector pLNx harbors the flycode library with a diversity of $10^8$ sequence variants (FIG. 2) and allows introducing a protein library of interest (PLOI) in frame with the flycodes. The result of this step is a "nested library" since two libraries (PLOI and flycode library) are nested into each other. The expression vector also allows restriction enzyme-mediated excision of the nested library (PLOI fused to flycodes), so that it can either be inserted into the deepsequencing plasmid or that direct Illumine MiSeq adaptor ligation can be performed using double-stranded oligonucleotides (adaptors). Note that the PLOI can be any genetically encoded library.

The PLOI is introduced into the expression vector by restriction digesting a source DNA that encodes the library, followed by ligation into the expression vector. The inventors use a type IIS restriction enzyme (SapI) for this purpose. The source DNA typically stems from a phagemid obtained after phage display selections, containing the SapI sites oriented such that the PLOI can be sub-cloned into the NestLink expression vector without PCR amplification (description of this vector, see below). When the PLOI is inserted, it replaces a negative selection cassette (ccdB), which greatly improves the efficiency of the insertion step.

The flycode is cleaved away from the PLOI by thrombin and the His-tag is removed from the flycode by trypsin. These cleavages ensure that peptides with optimal mass, optimal hydrophobicity and optimal charge are isolated for mass spectrometry (see flycode description above). It is also conceivable that any other combinations of proteases may be used for the same purpose.

Of note, the C-terminal arginine (R) of the flycode plays an important role: first, it is the only positively charged amino acid of the flycode, as lysines or other arginines are omitted in the flycode library. For this reason, trypsin—a protease that cleaves after positively charged residues and is therefore considered to be rather unspecific—can be used to specifically cleave the peptide bond between the arginine and the His-tag (the flycode would be rather too heavy with the His-tag for mass spectrometry analysis and the His-tag would reduce the separation in reverse-phase chromatography prior to mass spectrometry). Second, it is known that peptides with C-terminal arginines are particularly well detectable by mass spectrometry (favorable ionization properties). And third, because of this single positively charged amino acid present in the flycode, the total charge is consistently 2+(N-terminus+arginine, all other residues are neutral at the low pH of the detection), which facilitates data analysis.

An important aspect of the technology is the fact that it is possible (and necessary) to attach several unique flycodes to the same member of the protein library of interest. For example, to analyze a pool of 100 different proteins, 2000 flycodes are attached to these 100 proteins so that in average, each protein of the pool is linked 20 times to a different flycode (the ratio between pool members and flycodes can in fact be varied as desired). Redundant tagging facilitates the unambiguous detection of pool members through multiple flycode sequences and averages out potential influences of the flycode sequence to the biophysical properties of the analyzed proteins of interest. Redundant tagging also enables determination of relative quantities of different protein library members within a selected sample or of the same protein library member within differently selected samples. The redundancy is in addition required for technical reasons: although the flycodes are designed for optimal detection by mass spectrometry, some flycodes will not be detected because they will either be lost during sample preparation or not elute within the hydrophobicity window of the reversed phase column which is analyzed by mass spectrometry.

In addition the NestLink expression vector contains two SfiI restriction sites that allow excision of the nested library (PLOI fused to flycodes), so that it can either be inserted into the deepsequencing plasmid or that Illumina MiSeq adaptors can be ligated directly using double-stranded oligonucleotides (adaptors). The rationale for this crucial step is provided below.

Of note is that the SfiI restriction sites and\or other restrictions sites either within the PLOI or in between the PLOI and the flycode can be used to add additional sequences to the nested library. These additional sequences can hence be expressed as a fusion to the nested library (in between the flycode and the PLOI or adjacent to the nested library). Importantly, such sequences are not increasing the deepsequencing read length (which is limited due to technical reasons) as the transfer to the deepsequencing plasmid (or the direct deepsequencing adapter ligation via oligonucleotides) is performed before introducing these additional sequences. Furthermore, adding additional sequences in this way maintains the physical linkage between the flycode and the PLOI, which is absolutely crucial for a correct assignment of flycodes to PLOI-members.

Deep Sequencing Plasmids

The deep sequencing plasmids are a set of vectors that carry all necessary sequences for deep sequencing by Illumina MiSeq and that allow insertion of pools of nested library members from the NestLink expression vector.

Figure 1:
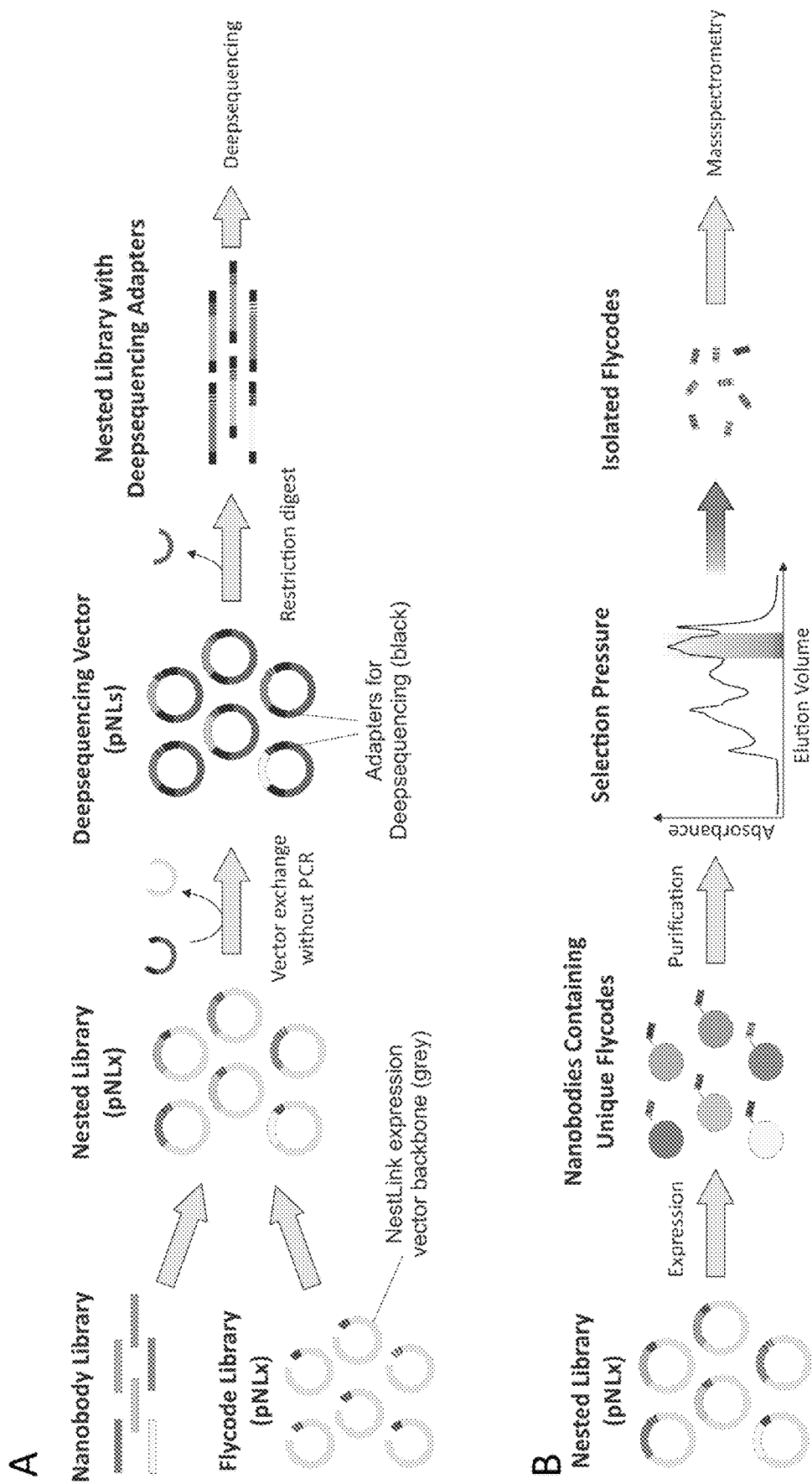
FIG. 1 shows an overview of the NestLink technology. A) A nanobody library is nested within a Flycode library encoded on the expression vector pNLx. Subsequently, the flycoded nanobody sequences are excised via restriction digest and inserted into pNLs, which results in the attachment of the required adapter sequences for deepsequencing. The adapters linked to the flycoded nanobodies are then excised via restriction digest and subjected to deepsequencing in the linear form. B) The nested library encoded in pNLx is expressed and purified. A selection pressure is applied (in this particular case, proteins with an apparent molecular weight of a nanobody monomer are selected via size-exclusion chromatography) and the Flycodes of the selected nanobodies are isolated via protease cleavage. C) The deepsequencing data allows generation of a database that assigns all Flycodes to their corresponding nanobody. The Flycodes of each nanobody are concatenated. The previously isolated Flycodes (see B) are subjected to LC-MS and peak lists of the recorded MS/MS data are generated. The MS/MS data is searched against the database containing the concatenated Flycodes, which allows identification and relative quantification of selected nanobodies.
Figure 1:
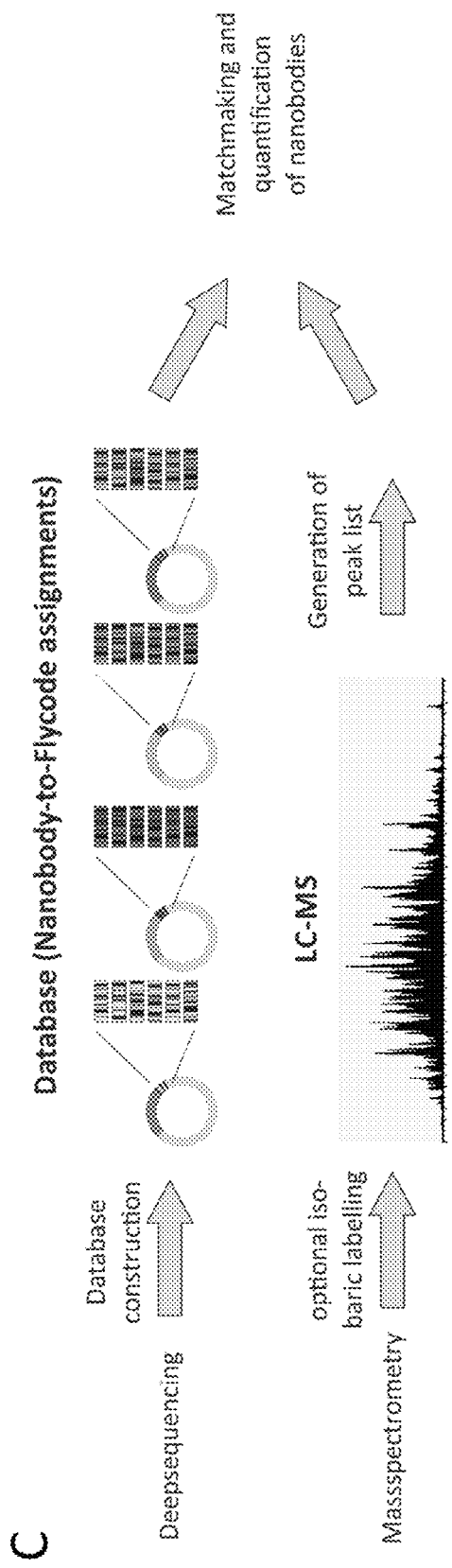

Transfer of the nested library into the deep sequencing plasmid (FIGS. 1 and 2) is performed via restriction digest and ligation. The inventors used the restriction enzyme SfiI for this purpose, as it possesses high enough specificity, which is crucial when digesting entire libraries that may encode restriction sites by chance. Furthermore, the chosen SfiI recognition site translates into reasonably flexible and hydrophilic amino acids that can be used as linker amino acids in the expression construct.

The inventors could show by experiments that it is crucial for NestLink that the transfer step from the NestLink expression vector into the deep sequencing plasmid does not include a PCR amplification step of the nested library. PCR amplification of the protein-flycode sequences inevitably leads to recombination of non-homologous regions (e.g. CDRs) between library members and of flycodes (the unintended attachment of the flycode of one protein of interest onto another where it was not attached to in the NestLink expression vector). Thereby the linkage between flycode and protein is destroyed.

As described above, the nested library is cut out from the expression vector via SfiI. Subsequently, it is ligated into the deep sequencing plasmid. It replaces a negative selection cassette (ccdB), which is crucial for the efficiency of the insertion step. After insertion, it is flanked by the sequences that are necessary (and frequently used) for deep sequencing by Illumina MiSeq. Sequencing takes place from both sides towards the center. The relevant regions are therefore present on both sides of the insert in opposite direction (reverse complement sequences, except index).

Here a description of the sequence from the inner part (the insert) towards the outer regions:

SfiI sites: Are used to replace ccdB by the nested library.

Diversity: The Illumina MiSeq technology generates the first sequencing signal based on the sequence next to the Primer binding site. The first few bases must be diverse (not identical) to prevent signal overload of detection channels and abortion of the sequencing run.

Primer binding site: Sequencing primer binds here.

Index (labelled with numbers 501 and 701): The Illumina MiSeq technology allows multiplexing, i.e. several samples can be analyzed in one sequencing run. To determine which reads belong to which sample an index (variable 8 bp stretch) is also read. In order to be able to sequence several NestLink experiments in a single deep sequencing run, the inventors generated a set of 11 deep sequencing plasmids, each carrying a different pair of indices (note that there's an index sequence on both sides of the insert).

Adapter: This is used to immobilize the DNA template for deep sequencing on the Illumina MiSeq flow-cell.

BseRI restriction site: This is used to create a linear DNA fragment, which is necessary for Illumina MiSeq deep sequencing. The fact that BseRI is a type IIS restriction enzyme (cleaves outside its recognition sequence) is particularly useful to minimize the overhang at the adapter.

In the traditional method, all these Illumina MiSeq sequence elements are attached to the DNA to be sequenced either by PCR, by ligation of Illumina adaptors, followed by PCR amplification or by the TRuSeq DNA PCR-free Sample Prep Kit (Illumina). In the inventors' protocol, the DNA to be sequenced (here the protein-flycode sequences) is subcloned from a donor vector (here the NestLink expression vector) into the deep sequencing vector by restriction and ligation, thereby avoiding PCR. In a final step, the deep sequencing vector is cleaved using BseRI. This releases the complete Illumina MiSeq sequencing template which is separated from the vector backbone by DNA agarose gel and purified by gel extraction.

Double-Stranded Adapter-Oligonucleotides for Deepsequencing

A second strategy allowing for PCR-independent attachment of the necessary adapter sequences for Illumina MiSeq deepsequencing to the PLOI relies on double-stranded oligonucleotides that carry the same set of adaptor sequences as described for the deepsequencing plasmids, which can be generated via gene-synthesis of complementary single-stranded oligonucleotides and a subsequent annealing reaction. The complementary single strands are synthesized with a difference in length, resulting in a sticky overhang of the annealed adapter. This overhang corresponds to the complementary sequences of the cut SfiI restriction sites, which is generated when the flycoded PLOI is excised from NestLink expression vector. The annealed oligonucleotides can therefore be ligated with high efficiency to the flycoded PLOI to attach adapter sequences required for Illumina MiSeq deepsequencing. The ligation product is purified via agarose gel prior to deepsequencing.

Here a description of the sequence of the final deepsequencing template from the inner part (the insert) towards the outer regions:

Flycoded PLOI: The flycoded PLOI is excised from the NestLink expression vector via SfiI restriction digest.

Remainder of SfiI restriction sites: This enzyme allows excision from the NestLink expression vector and the generated sticky ends are used to attach the deepsequencing adapters site-specifically.

Diversity: The Illumina MiSeq technology generates the first sequencing signal based on the sequence next to the Primer binding site. The first few bases must be diverse (not identical) to prevent signal overload of some detection channels and abort of the sequencing run.

Primer binding site: Sequencing primer binds here.

Index (labelled with numbers 501 and 701): The Illumina MiSeq technology allows multiplexing, i.e. several samples can be analyzed in one sequencing run. To determine which reads belong to which sample an index (variable 8 bp stretch) is also read. In order to be able to sequence several NestLink experiments in a single deep sequencing run, the inventors generated 7 deep sequencing adaptors (3 for the one end and 4 for the other end), which allows the generation of 12 different index pairs.

Adapter: This is used to immobilize the DNA template for deep sequencing on the Illumina MiSeq flow-cell.

Quantification of PLOI-Members Via Flycodes

Figure 3:
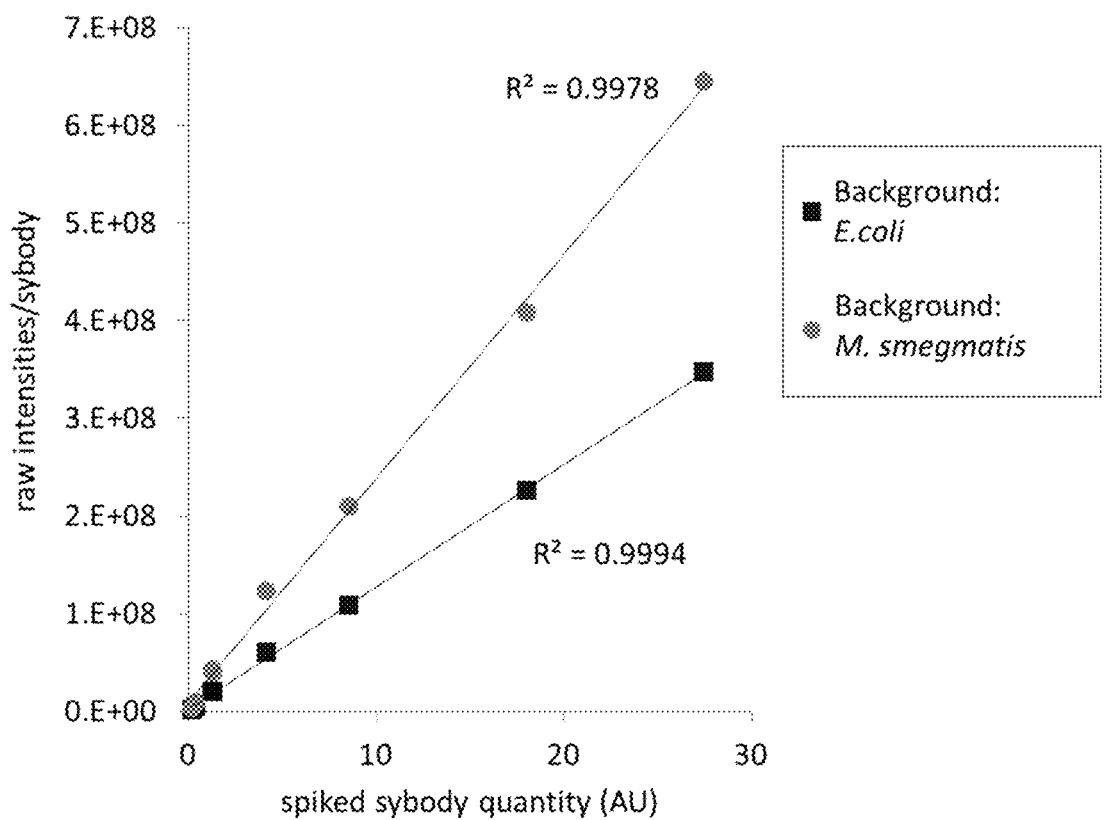
FIG. 3 shows absolute quantification of PLOI-members via Flycodes using LC-MS. Seven known quantities (x-axis) of flycoded sybodies were spiked into two different samples containing either lysate from *E. coli* or *M. smegmatis*, respectively (background). The flycoded sybodies were spiked at 0.2, 0.4, 1.3, 4.1, 8.5, 18.0 and 27.5 absorbance units (280 nm) and contained 28, 56, 112, 56, 112, 84 and 112 Flycodes as determined by deep sequencing. Isolated Flycodes were analyzed by LC-MS. The MS1 intensities from all Flycodes of each sybody were summed using the software Progenesis.

Many NestLink applications require the absolute quantification of flycoded PLOI-members. While LC-MS is inaccurate at quantification of individual peptides in proteomics, NestLink benefits from multiple Flycodes attached to each PLOI-member and from a homogenous Flycode library, which is designed for optimal detection by mass spectrometry. Based on this consideration, the inventors hypothesized that the summed MS1 intensities of all Flycodes of any given PLOI-member must be proportional to the quantity of this PLOI-member in a sample. The inventors tested this hypothesis by spiking known amounts of eight sybodies linked to variable numbers of Flycodes into two samples that contained lysates from *E. coli* and *M. smegmatis*, respectively (FIG. 3). The observed linear relationship between the summed MS1 intensities of all Flycodes of each flycoded sybody and its spiked quantity proved the correctness of the hypothesis and demonstrates that the NestLink procedure described herein, can be used to quantify individual PLOI-members within a pool. The absolute quantity of individual PLOI members can be determined if known amounts of one or more flycoded proteins (standards) are spiked into a sample before flycode isolation for LC-MS.

Phagemid for Phage Display Selections (Before NestLink)

In most of the inventors' current applications, the PLOI is a pool of enriched synthetic nanobodies, called sybodies. Typically, a large sybody library is enriched using phage display to bind to a target protein. In order to avoid recombination of non-homologous regions (i.e. the CDRs), the PLOI must not be amplified by PCR after phage display selections. To this end, the phagemid vector (FIG. 2A) was constructed such that the PLOI can be sub-cloned via SapI restriction sites into the NestLink expression vector. Of note, the SapI sites are part of the translation product, which is displayed at the phage surface. The inventors could show experimentally that these additional amino acids stemming from the SapI sites do not interfere with phage display efficiency.

Apart from the SapI sites, the phage display vector contains all elements typically present in phagemids used to display proteins on the M13 phage and is a derivative of the vector pMESy4 (genbank KF415192).

An additional general note relevant for all vectors described here: In order to allow an efficient transfer of an insert from one vector into another, it is crucial that the vectors carry different antibiotic resistances. Therefore the NestLink expression vector carries a chloramphenicol resistance marker and the deep sequencing vectors a kanamycin marker. Further, the phagemid for phage display selections contains an ampicillin resistance marker.

Proof of Concept Experiment

In this experiment, the inventors demonstrated that Nest-Link can be used to characterize individual proteins within a large pool of protein candidates in an unprecedented way and that the pool members with the most promising characteristics for downstream applications of choice can be identified.

More specifically, the proof of concept experiment described below, demonstrates that i) an efficient method for library nesting at well-controlled library diversities was developed and ii) that nested libraries can serve as a basis for unprecedented selection pressures on pools of binders.

In this example, the inventors worked with a PLOI consisting of a pool of sybodies that was pre-enriched via ribosome and phage display (not described) against maltose-binding protein (MBP)

The inventors used the NestLink method described in this patent to impose the following selection pressures on a diverse pool of sybodies at once: i) selection of the highest expressing sybodies, ii) selection of the sybodies with the highest solubility, and iii) selection of the sybodies that bind to the target in a solution binding assay.

Using the protocol described in the materials and methods section, the inventors intended to link about 1200 distinct sybody pool members to approximately 17,000 unique Flycodes, resulting in a so-called "nested library". This was carried out by first cultivating an appropriate clone number of cells containing sybody-encoding phagemids in one vessel, followed by isolation of their plasmid DNA. Instead of picking the sybody clones individually, the colony forming unit number (cfu) per volume of recovered bacteria was estimated after transformation via plating on agar plates. Hence, an appropriate volume of recovered bacteria (approximately 1,200 cfu) was used for inoculation of a culture that was subsequently harvested for plasmid DNA isolation. The DNA inserts of these diversity-restricted phagemids were then ligated to the expression vector pNLx containing the Flycode library of approximately $10^8$ distinct variants. Using cfu estimations as outlined above, the number of clones was restricted to approximately 17,000. Since only about 17,000 Flycode-containing vectors (as determined by cfu estimation) out of $10^8$ variants were used, the inventors calculated that 99.974% of Flycodes are unique and therefore, the vast majority of Flycodes are tagging one unique sybody. Furthermore, since they nested about 1,200 sybody genes within about 17000 Flycode-containing vectors, they expected that the average sybody was tagged with 14 different Flycodes.

The nested library in the vector pNLx was expressed in bacteria in a single flask and purified as a flycoded binder pool to perform selection experiments (see below). In order to sequence the nested library, flycoded sybodies were transferred to the deepsequencing vector pNLs that harbors all relevant sequences for Illumine deep sequencing using a MiSeq device. Deep sequencing of the nested library afforded an unambiguous assignment of every Flycode to its corresponding sybody.

The deepsequencing data was in agreement with the expected sybody and Flycode numbers within the nested library, as 1080 distinct sybody sequences, linked to 13,620 unique Flycodes were obtained after data filtering. On average each sybody was therefore linked 12.61 times to a different and Flycode. The inventors did not observe ambiguous Flycode linkage to sybodies after sequencing data filtering (i.e. the same Flycode attached to two or more different sybodies). This successful attempt to nest libraries within each other using well controlled diversities is unprecedented according to the inventors' knowledge.

Using the deepsequencing data, a database harboring the entire sequence information of the nested library was constructed by concatenation of all Flycodes of each sybody into a theoretical continuous protein sequence with the corresponding sybody as an identifier. This database was then uploaded on a Mascot-server, for later usage in MS/MS ion searches As an example for a novel application of this technology, the inventors used the nested library and selected and identified specifically those sybodies with a certain apparent hydrodynamic radius and those which exhibited a high affinity interaction to MBP in solution. Both of these characteristics were determined by size-exclusion chromatography (SEC) and are not amenable using current state-of-the art display systems that require a genotype-phenotype linkage, because the genotype increases the size of the displayed protein usually by more than 100-fold, rendering the display-particle insensitive to small size differences at the protein level.

To this end, the nested library was expressed and flycoded binders were purified via Ni-NTA resin and subjected to SEC. The eluted fractions of sybodies that corresponded to monomeric proteins (the binder candidates with the highest solubility) were pooled and split into two equivalent aliquots. One aliquot was incubated with MBP and the other with buffer only. The two samples were analyzed separately on SEC (the run without MBP was used as a control) and the elution fractions corresponding to the size of the sybody-MBP complex were collected. The Flycodes of the collected fractions of the MBP and of the control run were subsequently isolated and subjected to either two separate LC-MS runs or combined into one LC-MS/MS run after isobaric tag labelling of the isolated Flycodes. The previously generated deepsequencing database (Flycode to sybody assignments) could then be used to identify the Flycodes in a Mascot search, thereby unambiguously identifying sybodies eluting at the size of the sybody-MBP complex. This experiment allowed the inventors to identify more than 300 unique sybodies, which are all well expressed, monomeric and bind the target protein in solution.

Applying NestLink for Off-Rate Determination

Figure 4:
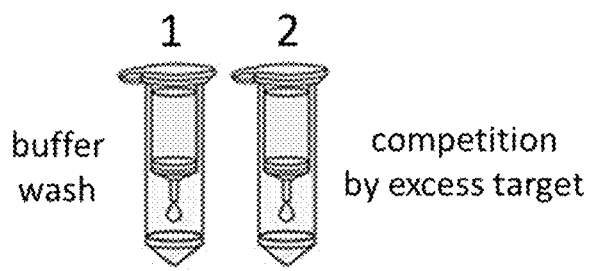
FIG. 4 shows identification of sybodies exhibiting the best off-rates from 1,080 candidate binders via NestLink. A: Monomeric sybodies co-eluting with the biotinylated target protein in solution (SEC) were immobilized on two equivalent streptavidin sepharose columns. One column was washed with buffer, the other column was washed by an excess of non-biotinylated target for 3 min. Subsequently, the Flycodes of the remaining bound sybodies were isolated and quantified via LC-MS1 intensities. B: the LC-MS1 intensities (sum over all flycodes) were determined for each pool member and the ratio between the two columns was plotted on the y-axis for each individual sybody (x-axis). Sybodies, which were not expressed, not monomeric or not binding to the target in solution were not detectable on either of the columns, as they were removed as a result of the pre-selection pressures described in the proof of principle experiment (sybodies 320-1,080). Weakly binding sybodies were only detectable after the buffer wash, but not under competition with excess target (sybodies 187-320). Sybodies 1-186 were detected on both columns and were ranked according to their off-rate. The most promising sybodies for downstream applications are the ones with the slowest off-rates resulting in a ratio close to 1. C: Correlation of NestLink readout and SPR experiments of individually picked sybodies. DNA sequences of 11 sybodies analyzed in B) were synthesized (gene synthesis) and the corresponding binders were expressed, purified and analyzed by surface plasmon resonance one-by-one. The SPR data are plotted as the residual binding signal after 3 minutes of washing (as a measure of the off-rate) on the x-axis versus the sybody ratio determined by NestLink as shown in B) on the y-axis.
Figure 4:
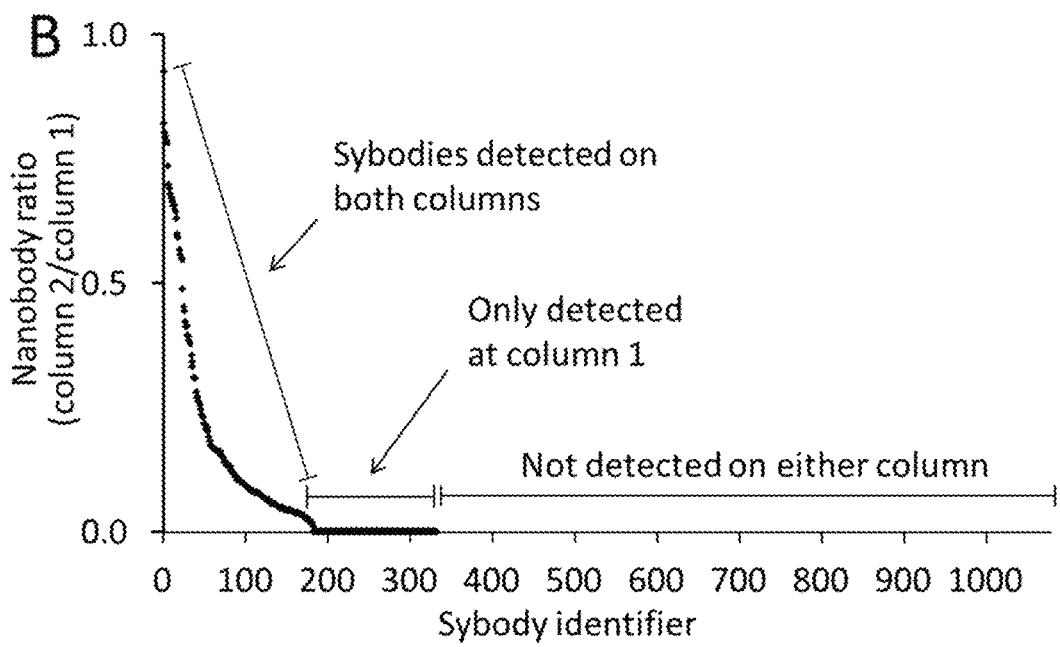
Figure 4:
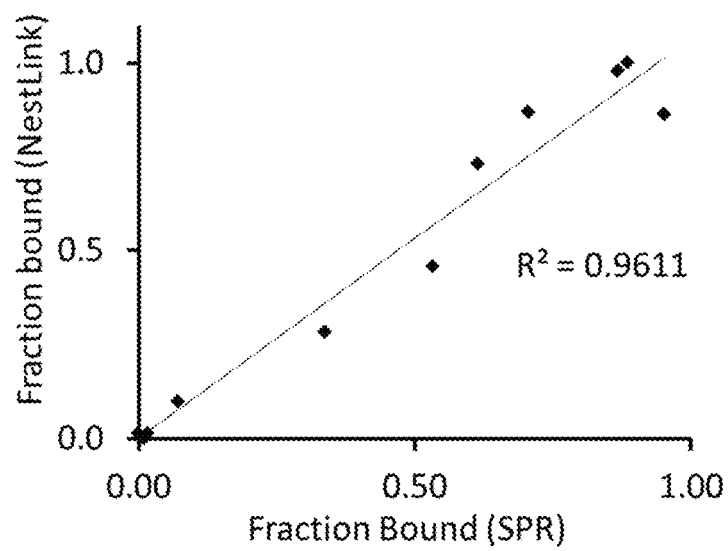

In order to score MBP-specific sybodies, which were identified in the above-described proof of principle experiment, according to their binding off-rates, the inventors immobilized equal amounts of the isolated MBP-sybody complexes via the biotinylated MBP on two streptavidin-sepharose columns (FIG. 4). An off-rate selection with excess non-biotinylated MBP (wash for 3 min) was then performed at one column, while the other column was washed by buffer only. After the washes, the remaining sybodies from both columns were eluted and their Flycodes were subjected to two LC-MS/MS runs. Similar to the above-described in-solution binding experiment (SEC runs), the deepsequencing database was used in Mascot searches for sybody identification via the Flycodes. In addition, the MS1 intensities of all identified Flycodes were summed up for each sybody using the Progenesis software. Due to the quantitative nature of MS1 peak intensities as determined above, the inventors expected that the ratio between the flycode-intensity-sums for each sybody between the two columns would correspond to their relative concentrations before and after the off-rate selection with excess non-biotinylated target. Assuming that each dissociation reaction follows a single-exponential decay and using the knowledge about the washing time with excess target (3 min), the authors were therefore able to determine the approximate off-rates for more than 300 binders at once. This analysis was confirmed by measuring the off-rates of 11 individual binders using surface plasmon-resonance. Determining off-rates within a pool of binder candidates in a single experiment is unprecedented according to the author's knowledge. A process which required several weeks previously due to the necessity for processing individual proteins can now be performed at once using the technology described herein.

Applying NestLink for Binder Identification from Immunized Camelids

NestLink was applied to a pool of natural nanobodies, which was obtained via cDNA isolation from B-cells of an immunized alpaca (camelid). The antigen used for the immunization was TM287/288, an ABC transporter (integral membrane protein) from *Thermotoga maritima*. Opposed to the traditional protocol of nanobody generation from camelids, this nanobody pool was not enriched against the target using phage display.

Figure 5:
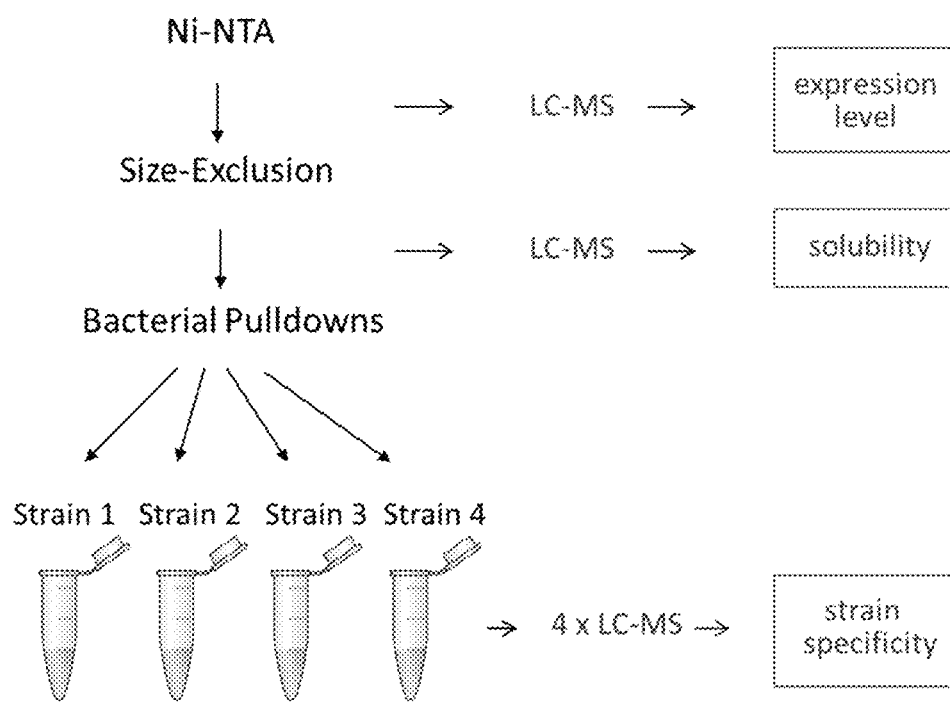
FIG. 5: Analysis of 3,469 nanobodies from an immunized alpaca and identification of those, which exhibit the strongest antigen binding in solution. After eliminating those pool members with poor expression levels (step 1) and solubility (step 2, selection of monomeric nanobodies), the monomeric fraction of the pool was incubated with the membrane protein antigen at three different stoichiometric ratios and analyzed via SEC. LC-MS samples were collected after step 1 (reporting on the expression level of each individual pool member), at step 2 (reporting on the solubility or each individual pool member) and from all target/complex peaks at step 3. The pie charts represent the relative amount of each nanobody in the pool (non-binders or weak binders collectively colored light gray, total amount of pool members corresponds to 100%) at the different stages of the selection procedure, as determined by the sum of all MS1 intensities for each nanobody (100%=sum of all MS1 intensities of all flycodes of all nanobodies). As expected for step 3, an increase of the pool to antigen ratio leads to an increase in internal competition of the many binding pool members for the limited amount of antigen. The fraction of pool members with the strongest affinity therefore increases at higher competition for the limited epitopes.
Figure 5:
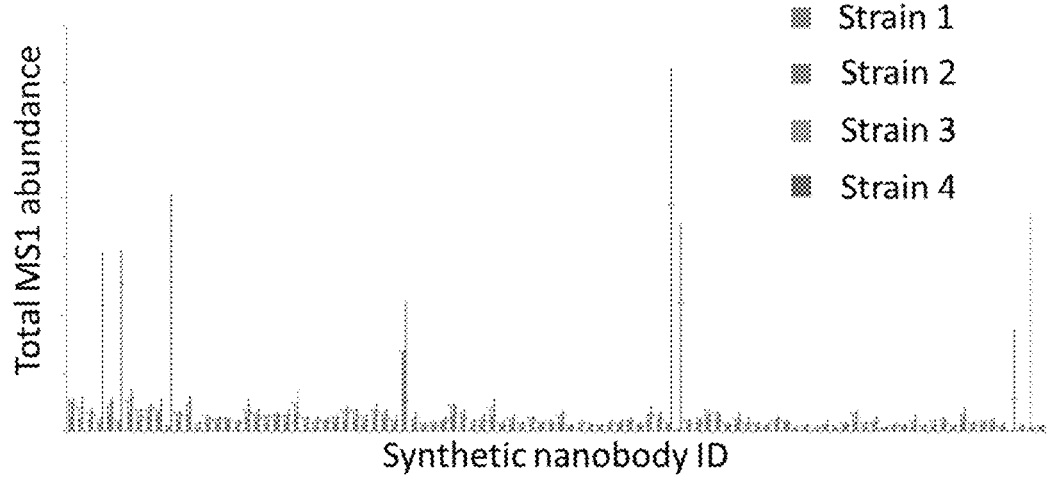

The nanobodies were PCR amplified, diversity restricted and interlaced with the Flycode library to yield 3,469 unique nanobody sequences attached to 59,974 unique Flycodes as determined by Illumine MiSeq deepsequencing (see materials and methods section). The nested library was expressed and purified via Ni-NTA, followed by isolation of the monomeric pool members via SEC. Analogously to the proof of principle experiment (described above), the unfavourable binder candidates, which did not express or which were not soluble, were eliminated in these pre-selection steps. LC-MS sample were collected after the elution from the Ni-NTA column and from the monomeric fraction of the SEC run. Subsequently, increasing amounts of the pool were incubated with TM287/288 at ratios of approximately 0.1:1, 2:1 and 100:1 and antigen/pool mixtures were subjected again to three SEC runs (FIG. 5). The fractions corresponding to the size of the target/nanobody complex were collected. The Flycodes of all collected samples were separately isolated and analysed by LC-MS/MS, which allowed comparison of expression levels, solubility (monomeric on SEC) and binding strength to the antigen in solution for all binders at once.

In this analysis of 3,469 unique nanobodies from an immunized camelid, the inventors identified 27 high-affinity binder families with favourable stability, expression levels and solubility. Remarkably, NestLink was much more efficient than phage display selections and excessive conventional screens, using ELISA and Sanger-sequencing, which identified only 5 of these families in the same pool within a significantly longer processing time. In summary, it can therefore be stated, that NestLink can be used to identify the most promising candidate biomolecules from immunized camelids, with a throughput and accuracy unmet by current state-of-the-art procedures.

Applying NestLink to Identify Binders Targeting a Protein at the Cell Surface

The experiments described above were performed with the goal of identifying binding proteins against purified targets/antigens in solution, which yielded favourable research tools for in vitro applications, such as crystallography. Here, the inventors intended to resolve a core bottleneck of drug development, which is the identification of membrane protein binders that recognize the target protein with high specificity and affinity at the cell surface. Developing a biomolecular drug against a membrane protein target typically requires two consecutive steps, which are fundamentally different. First, a diverse pool of binder candidates is generated via display procedures or immunization. Second, the diverse pool is screened for binding and function in cellular assays. The latter is inherently inefficient and slow because it requires analysis of individual binder candidates one by one (typically in a miniaturized format). In this experiment, the inventors replaced the second (screening) step by NestLink, in order to identify cell-surface binders, specific against an integral membrane protein target without the laborious analysis of individual binder candidates one by one.

Figure 6:
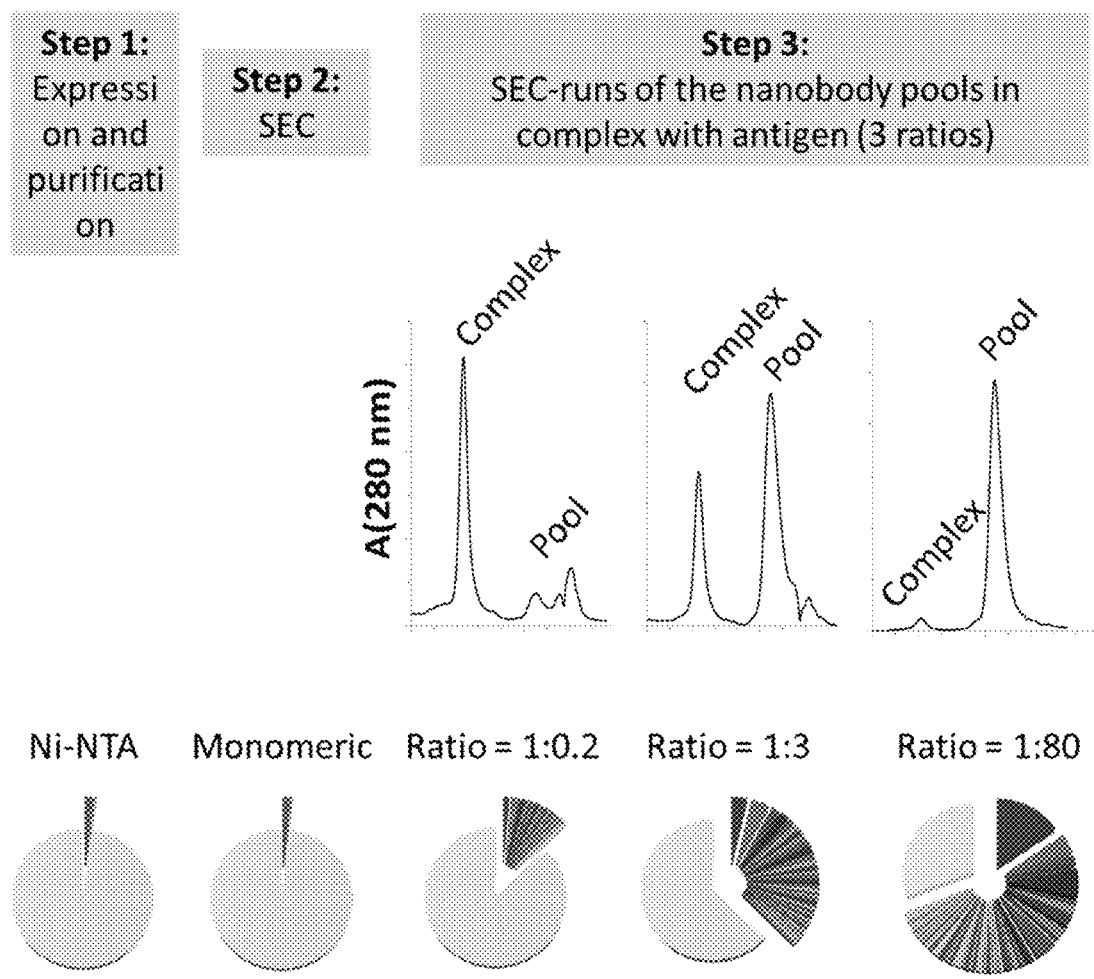
FIG. 6: A: Analysis of 1,456 sybodies from a pool generated by in vitro selections (step 1) against a purified outer membrane protein target, for cell surface binding at Gram-negative bacteria of interest (step 2). In step 2 (NestLink), those pool members with poor expression levels and solubility were first eliminated from the ensemble, followed by 4 different pull-down experiments using 4 different bacterial strains of interest. After removal of pool members by washing that did not bind with high affinity to the cells, all Flycodes of the pool were isolated and analyzed by LC-MS. The sum of all MS1 intensities of all Flycodes per sybody could then be used as a measure for the relative concentration of each individual sybody in the pool at each of the target cells. This allowed for an unambiguous cell-specificity readout (B) reporting for each sybody (x-axis) its relative concentration (compared to the entire pool) at each of the 4 cell types. For clarity reasons, only 25% of all analysed sybodies are shown in B.

The inventors first performed in vitro display of a sybody library against a pure, detergent-solubilized outer membrane protein antigen of a Gram-negative bacterium (step 1, generation of a diverse pool of binder candidates). Instead of testing each individual binder candidate of this diverse pool individually for cell-surface binding (normally step 2), the inventors performed NestLink and tested a large pool of candidates at once (FIG. 6A). 1,456 sybodies were interlaced with the flycode library, resulting in the linkage of 31,500 Flycodes (on average 22 Flycodes/sybody). As described above, the flycode-to-binder assignment was obtained via deepsequencing and the nested library was expressed, purified and the monomeric pool members were isolated (counter-selection/elimination of undesired binder candidates). Hence, pool members with poor expression levels and poor solubility were first eliminated and the expression levels and solubility characteristics of each pool member was monitored. The NestLink process thus funneled exclusively promising binder candidates into the cell-surface selection, which was performed as follows: the monomeric pool members were split into 4 equivalent fractions and each fraction was incubated with another bacterial strain. Non-binding sybody candidates were removed by pelleting and resuspension/wash using buffer. Subsequently, all Flycodes of sybodies that bound to one of the bacterial strains were isolated and subjected to LC-MS analysis. The sum of all MS1 intensities of all Flycodes per sybody was used as a measure for the relative concentration of each individual sybody in the pool at each of the target cells. This allowed for an accurate cell-specificity readout (FIG. 6B).

From 1,456 binder candidates in the pool, 6 well-expressed and soluble sybodies were identified, which specifically recognized the protein target in its native form embedded in the outer membrane of the Gram-negative bacterium of interest (strain 4). The inventors confirmed this finding by individually analyzing these 6 identified sybodies by flow-cytometry against the 4 strains (after labelling them fluorescently). All tested candidates exhibited the same specificity profile in this single-clone assay, as it was observed via NestLink. Of note, each of the identified binders was only present to <0.05% in the nested pool, as determined by Illumina MiSeq deepsequencing. Considering that state-of-the-art screens only take one characteristic of a binder candidate into account (e.g. target binding), but fall short in reporting expression levels or solubility/oligomerization propensities, it is unlikely that any of these six binders could have been identified by a classical single clone screening approach. Hence, this experiment demonstrates that NestLink permits to screen binder libraries at unprecedented depth thanks to the absence of a genotype-phenotype linkage and the interlacement of two libraries.

Applying NestLink to Monitor Biodistribution and Pharmacokinetic Parameters in Model Organisms In the previous examples, the inventors showed that NestLink selection allow for unprecedented selection pressures, due to the absence of the genotype-phenotype linkage (e.g. selection of monomeric pool/library members on SEC). Here, another selection pressure is introduced, which cannot be achieved in the case of a physical genotype-phenotype linkage: the selection of proteins with particular biodistribution and pharmacokinetic properties in living organisms. A nested (flycode-tagged) pool of biomolecular therapeutic candidates may be injected into an animal model and the relative concentration of each pool member may be measured after a certain elapsed time at each location in the body (e.g. at different organs, tissues or tumors, etc.) by LC-MS. An analysis of this type would result in a comprehensive/global biodistribution analysis for each individual pool member within the body at one specific time-point. If several analogous individuals of the same species were subjected to this analysis after various different time points, the NestLink biodistribution analysis may be extended into the time dimension, thus allowing for the pharmacokinetic data acquisition at low or medium temporal resolution for each candidate.

The inventors set the basis for this type of analysis by testing and optimizing Flycode extraction procedures from homogenized mice tissues that were previously spiked with different amounts of flycoded sybodies. In detail, several sybodies were first linked to a small number of Flycodes (20-30) and the sybody-to-flycode assignment was determined by Illumina MiSeq deepsequencing. The Flycode-tagged sybodies were then expressed and purified individually and their concentration was determined by absorbance measurements. The individual sybodies were then combined at different concentrations (which were spanning an order of magnitude).

In parallel, frozen organs (liver, lung, kidney) and blood of mice were thawn and homogenized using denaturing buffer conditions and a potter. The previously prepared titration mix was spiked into the homogenates and incubated for 30 min at room temperature to allow potential proteases or flycode-modifying enzymes to act. Subsequently the sybodies along with their remaining Flycodes were extracted, the Flycodes were isolated by protease cleavage and analysed via LC-MS. Based on the detection of individual sybodies of the titration mix the inventors found that sybody detection via LC-MS from such homogenized organs and tissues is typically reliable down to the quantity of 30-100 ng (sybody). Given that up to 1 mg of therapeutics can typically be injected in a mouse model, it is clear that at most relevant locations in the body, dozens of micrograms will be present after injection of a nested pool. Hence, enough non-degraded and non-modified Flycodes are present to monitor global biodistributions and to conduct pharmacokinetic analyses of a binder pool.

Materials and Methods

In the following, a general protocol of the NestLink method is provided. It encompasses all steps required to carry out the experiments as outlined above and provides details concerning library nesting, deepsequencing, expression and purification of flycoded binder pools, Flycode extraction, LC-MS and data analysis.

Cloning of Flycoded Nanobodies by Library Nesting

1. Diversity Restriction of Sybody/Nanobody Pool

NestLink experiments have been carried out with pools of sybodies or natural nanobodies, which were obtained from in vitro binder selections by phage display or immunizations, respectively. In case phage display was used for binder selection, 200 ng of the in vitro selected pool of potential binders encoded in a phagemid was transformed into 50 μl of *E. coli* MC1061 chemically competent cells (competence achieved by protocol of Promega Corporation, Subcloning Notebook 2004). A dilution series was plated on agar plates containing 120 μg/ml ampicillin and incubated over night at 30° C. The colonies of a plate containing the desired colony forming units (in the above examples the number ranged between 1000 and 1500 cfu) was resuspended by 2 ml of LB medium containing 100 μg/ml ampicillin and the suspension was transferred to a 200 ml culture of LB-medium containing 100 μg/ml ampicillin. This culture was grown over night at 37° C. and was used for DNA preparation (Kit: #740412.10, MACHEREY-NAGEL). 15 μg of the prepared phagemid was digested by 100 units of BspQI (New England Biolabs, # R0712L) in buffer NEB 3.1 (New England Biolabs, # B7203S) in a reaction volume of 140 μl at 50° C. for 1 h, followed by heat inactivation of the enzyme at 80° C. for 20 min. Electrophoresis on a 2% (w/v) agarose gel was performed and the band corresponding to the binder pool was excised and extracted (Kit: #740609.250, MACHEREY-NAGEL). In case of immunized alpacas, the nanobody sequences were amplified from cDNA of B cells as described (Pardon et al., Nat Protoc., 2014 March; 9(3):674-93) and amplified with primers containing BspQI restriction sites. 5 μg of the purified PCR product was digested by 100 units of BspQI (New England Biolabs, # R0712L) in buffer NEB 3.1 (New England Biolabs, # B7203S) in a reaction volume of 140 μl at 50° C. for 1 h, followed by heat inactivation of the enzyme at 80° C. for 20 min. Electrophoresis on a 2% (w/v) agarose gel was performed and the band corresponding to the binder pool was excised and extracted (Kit: #740609.250, MACHERY-NAGEL). The digested PCR fragment was cloned into the FX cloning initial vector with a Kanamycin resistance marker (Geertsma et al., Biochemistry, 2011 Apr. 19; 50(15):3272-8) and 3.500 cfu were resuspended by 2 ml of LB medium containing 50 µg/ml kanamycin and the suspension was transferred to a 200 ml culture of LB-medium containing 50 µg/ml kanamycin. This culture was grown over night at 37° C. and was used for DNA preparation (Kit: #740412.10, MACHEREY-NAGEL). 15 µg of the prepared phagemid was digested by 100 units of BspQI (New England Biolabs, # R0712L) in buffer NEB 3.1 (New England Biolabs, # B7203S) in a reaction volume of 140 µl at 50° C. for 1 h, followed by heat inactivation of the enzyme at 80° C. for 20 min. Electrophoresis on a 2% (w/v) agarose gel was performed and the band corresponding to the binder pool was excised and extracted (Kit: #740609.250, MACHERY-NAGEL).

2. Attachment of Flycodes to Sybody/Nanobody Pools and Flycode-Diversity Restriction The vector pNLx containing the Flycode library was digested by BspQ1, as described above for the phagemid and electrophoresis on a 1% (w/v) agarose gel was performed. The band corresponding to the opened vector was excised and extracted (Kit: #740609.250, MACHERY-NAGEL). 200 ng of the binder pool was ligated to 400 ng of digested pNLx using 2.5 units of T4 ligase (Fermentas #EL0011) in T4 ligase buffer (Fermentas #B69) in a reaction volume of 28 µl at 37° C. for 1 h, followed by heat inactivation at 65° C. for 10 min. 25 µl of the ligation reaction was used for transformation into 150 ul of electro-competent E. coli MC1061 cells (prepared according to Howard and Kaser 2007, Making and using antibodies, page 170). The cells were recovered for 30 min at 37° C. in SOC medium and a 200 ml culture containing 25 µg/ml chloramphenicol was inoculated with a volume of the recovered bacteria that corresponded to the desired number colony forming units as determined by plating of a diluted sample on an agar plate containing 25 µg/ml chloramphenicol (in the above examples the cfu number ranged between 13,000 and 30,000). The culture was grown over night at 37° C., followed by DNA preparation (Kit: #740412.10, MACHEREY-NAGEL) and the generation of a glycerol stock containing 1 ml of stationary phase culture mixed with 1 ml of 50% (v/v) glycerol.

Deepsequencing

1. Attachment of Illumina Adapter Sequences

15 µg of pNLx containing the flycoded binders was digested by 120 units of SfiI (Fermentas # ER1821) in Buffer G (Fermentas # BG5) in a reaction volume of 140 ul at 50° C. for 3 h, followed by the addition of 12 µl of 0.5 M EDTA for enzymatic inactivation. Electrophoresis on a 2% agarose gel was performed and the band corresponding to the binder pool linked to the Flycodes was excised and extracted (Kit: #740609.250, MACHERY-NAGEL). For the first example with the anti-MBP sybodies, the vector pNLs containing the adaptors relevant for DNA deepsequencing via Illumina MiSeq with an appropriate index (in this case 502 and 703 was used for dual indexing) was digested by SfiI, as described for pNLx above, and electrophoresis on a 1% agarose gel was performed. The band corresponding to the vector backbone was excised and extracted (Kit: #740609.250, MACHERY-NAGEL). 400 ng of the flycoded binder pool was ligated to 300 ng of digested pNLx using 2.5 units of T4 ligase (Fermentas #EL0011) in T4 ligase buffer (Fermentas #B69) in a reaction volume of 28 µl at 37° C. for 1 h, followed by heat inactivation at 65° C. for 10 min. 25 µl of the ligation reaction was used for transformation into 250 µl of electro-competent E. coli MC1061 cells (prepared according to Howard and Kaser 2007, Making and using antibodies, page 170). Cells were recovered for 45 min at 37° C. in SOC medium and a 200 ml culture containing 30 ug/ml kanamycin was inoculated with all recovered cells. A test sample was plated on kanamycin-selective agar plates in order to confirm that the ligation and transformation efficiency was sufficient for transfer of the entire nested library (>200,000 cfu in total). The culture was grown over night at 37° C., followed by DNA preparation (Kit: #27106, QUIAGEN). A restriction digest of 1 µg of the prepared pNLs containing the flycoded binder pool was performed using 5 units of BseRI (New England Biolabs, #R0581S) in CutSmart buffer (New England Biolabs, #B7204S) in a total reaction volume of 20 µl for 37° C. for 2 h, followed by heat inactivation at 80° C. for 20 min. Note that at this point several flycoded pools against various targets can be pooled (prior to the BseRI digest), each placed in a differently indexed pNLs. The insert containing the flycoded binder pool attached to the MiSeq adapters was subsequently extracted from a 1% agarose gel.

For the other examples provided above, 300-400 ng of annealed oligonucleotides containing sticky SfiI overhangs were mixed with 600 ng of the flycoded binder pool excised from pNLx by SfiI using 5 units of T4 ligase (Fermentas #EL0011) in T4 ligase buffer (Fermentas #B69) in a reaction volume of 20 µl at 37° C. for 1 h, followed by heat inactivation at 65° C. for 10 min. The flycoded binder pool attached to the MiSeq adapters was subsequently extracted from a 2% agarose gel (Kit: #740609.250, MACHERY-NAGEL). Note that at this point several flycoded pools against various targets can be pooled, each containing a different pair of ligated adaptors.

2. Determination of Nanobody-Flycode Linkages

Deepsequencing was performed on a MiSeq device from Illumina using a paired-end protocol (MiSeq Reagent Kit v2 (300-cycles)). In a first step of the analysis, the paired-end reads were stitched together using standard software (Illumina). For any given index pair, a total of 800,000-8 Mio reads were obtained, which corresponds to an average read redundancy of 25-70 (this number equals the total read number divided by the total expected flycode number for a given nested library). Using a custom-made script, the resulting raw reads were filtered by applying the following positive criteria: i) correct flanking pattern of invariable parts of the Flycode, ii) correct flanking pattern of invariable parts of nanobodies, iii) sequence does not contain N, iv) sequence is within the expected size range of possible nanobody-Flycode fusions, v) sequence of the nanobody-Flycode fusion is in frame (i.e. can be divided by 3) vi) sequence is devoid of stop-codons. After filtering, a list of unique Flycodes was generated. Flycodes which were read at least five times were considered to be correct. For each correct Flycode, a consensus sequence of all linked nanobody sequences was generated. The consensus sequence approach was required to correct sequencing errors in the nanobody sequence. A consensus score was introduced to monitor the variability among the nanobody sequences attached to the same Flycode. The score gives large penalties in case one or several nanobodies attached to the identical Flycode are clearly different from the others, thereby removing Flycodes linked to two or more different nanobodies from further analysis. Only nanobody-Flycode pairs with a high consensus score were considered further. In a final step, identical (consensus) nanobody sequences and all its linked Flycodes (in average 12-40 Flycodes per nanobody in the above examples) were identified. All Flycodes connected to the same nanobody were concatenated into a hypothetical protein sequence using the nanobody sequence as an identifier and this database was saved in fasta-file format.

Expression and Purification of Monomeric Flycoded Sybodies/Nanobodies

The E. coli MC1061 glycerol stocks containing pNLx harboring the flycoded binder pool were used for inoculation of a 50 ml LB preculture containing 1% glucose, which was cultivated over night at 37° C. 600 ml TB culture was inoculated by the preculture to an OD of 0.05 and cultivated for 1.5 h at 37° C. followed by culturing over night at 20° C. Induction was carried out at $OD_{600}$ of 0.8 by 0.05% (w/v) arabinose. Cells were harvested by spinning at 5,000 g for 20 min. The supernatant was decanted and the cells resuspended in 25 ml of 50 mM Tris-HCl pH 7.5 (20° C.), 150 mM NaCl, 15 mM imidazole pH 8.0 (20° C.), supplemented with a pinch of DNaseI (SIGMA #DN25). Cells were lysed using a microfluidizer (Microfluidics #110P) at 30,000 psi for two rounds, while cooled on ice. The cell debris was pelleted at 5,000 g for 30 min and the supernatant was applied onto a 1.5 ml Ni-NTA superflow column (QUIAGEN #1018142) by gravity flow. The column was washed by 30 ml of wash buffer containing 20 mM Tris-HCl pH 7.5 (20° C.), 150 mM NaCl and 30 mM imidazole pH 8 (20° C.). It was eluted by 6 ml of 20 mM Tris-HCl pH 7.5 (20° C.), 150 mM NaCl and 300 mM imidazole pH 8 (20° C.). 5 ml of the elution was injected onto a HiLoad 16/600 Superdex 200 µg (GE Healthcare Life Sciences #28989335) and the region corresponding to the monomeric fraction was collected and concentrated to a volume of 1.2 ml at an absorbance (280 nm) of 2.1 at a Nanodrop 2000c (Thermo Scientific) against buffer for further selection experiments as outlined in the above examples.

Isolation of Flycodes

Flycoded PLOI containing samples were diluted 10-20 times by Buffer Ex (20 mM Tris-HCl pH 8.5, 150 mM NaCl, 0.5% (v/v) Triton X-100, 0.125% (w/v) sodiumdeoxycholate, 10 mM imidazole pH 8.0, 4.5 M GdmCl), filtered (syringe filter 0.2 µm cutoff) and incubated with 100 ul of Ni-NTA superflow slurry (QUIAGEN #1018142) for 2 h at room temperature. The resin was subsequently pelleted at 500 g for 10 min and transferred to a mini bio-spin chromatography column, followed by 3×500 µl washes using buffer Ex, 3×500 µl using buffer TH (20 mM TEAB pH 8.0, 150 mM NaCl, 2.5 mM $CaCl_2$) containing 30 mM imidazole pH 8.0 and 3×500 µl buffer TH. After closing the bottom end of the column the resin was resuspended in 100 µl buffer TH containing 2.4 U of Thrombin (MILLIPORE #69671-3) followed by incubation over night at room temperature. The column was then drained and washed by 3×500 µl buffer TH containing 30 mM imidazole pH 8.0, followed by 3×500 µl buffer TRY (20 mM TEAB pH 8.0, 50 mM NaCl, 2.5 mM $CaCl_2$) and elution by buffer TRY containing 300 mM imidazole pH 8.0. The eluate was spun (15,000 g) through a pre-equilibrated ($H_2O$) Microcon 10 kDa cutoff concentrator (AMICON: YM-10) and 1 µg trypsin (PROMEGA #V5113) was added to the filtrated followed by incubation over night at 37° C.

Eluted Flycode samples were subsequently subjected to a ZipTip (MILLIPORE #ZTC18S960) clean-up procedure. ZipTips were pre-washed by 200 µl methanol, 200 µl of 60% (v/v) acetonitrile (ACN) and 200 µl of 3% (v/v) acetonitrile containing 0.1% (v/v) of trifluoroacetic acid. 100 µl of the Flycode sample was loaded, followed by washing with 200 µl of 3% (v/v) acetonitrile containing 0.1% (v/v) of trifluoroacetic acid and elution by 2×40 µl of 60% (v/v) acetonitrile containing 0.1% (v/v) of trifluoroacetic acid. The solvent was subsequently evaporated (speedvac) and the Flycodes were resuspended in 15 µl of 3% (v/v) acetonitrile containing 0.1% (v/v) formic acid.

LC-MS

Using an Easy-nLC 1000 HPLC system, 2 µl of the resuspended Flycode solution was injected onto an in-house made capillary column packed with reverse-phase material (ReproSil-Pur 120 C18-AQ, 1.9 µm; column dimension 150 mm×0.075 mm). The column was equilibrated with solvent A (0.1% formic acid (FA) in water). Peptides were eluted with a flow rate of 0.3 µl/min using the following gradient: 0-60 min; 5-20% B (0.1% FA in ACN), 60-70 min; 20-97% B. After 10 min of washing by 97% B, the column was re-equilibrated by solvent A for 5 min. High accuracy mass spectra were acquired with an Orbitrap Fusion mass spectrometer (Thermo Scientific) using the following parameter: scan range of 300-1500 m/z, AGC-target of 5e5, resolution of 120,000 (at m/z 190), and a maximum injection time of 100 ms. Data-dependent MS/MS spectra were recorded in top speed mode in the linear ion trap using quadrupole isolation (1.6 m/z window), AGC target of 1e4, 35 ms maximum injection time, HCD-fragmentation with 30% collision energy, a maximum cycle time of 3 sec, and all available parallelizable time was enabled. Mono isotopic precursor signals were selected for MS/MS with charge states between 2 and 6 and a minimum signal intensity of 5e4. Dynamic exclusion was set to 25 sec and an exclusion window of 10 ppm. After data collection peak lists were generated using Proteome Discoverer 1.4 (Thermo Scientific).

Data Analysis and Quantification

LC-MS runs (one run per flycode extraction/sample) were pre-inspected by the software Xcalibur and Xcalibur raw-files were imported and converted by Progenesis to mznld-files. Progenesis was subsequently used to align LC-MS runs of interest (alignment score >80%) and remove peptide ions of charges +1 and +5 to +20 from the analysis. A combined mgf-file of all aligned LC-MS runs was subsequently exported from Progenesis (rank threshold <5, ion fragment count>1,000, deisotoping and charge deconvolution) and uploaded to the mascot server together with the previously determined flycode to PLOI-member assignment (deepsequencing database in fasta-file format, see above). The Mascot-identifications were directly imported into the software Scaffold, followed by data conversion and export of the spectrum report, which was subsequently imported into Progenesis, allowing assignment of features to their corresponding flycodes. Using Progenesis, the feature intensities were typically normalized to spiked standards and all unique flycodes of each PLOI-member were used for quantification. Raw and normalized intensities were subsequently exported (CSV format) and further analyzed by Excel.

The invention claimed is:

1. A mass spectrometry fragmentation based method for selecting a polypeptide from a library of polypeptides, comprising:
   a. deep sequencing a tagged nucleic acid library,
      wherein the tagged nucleic acid library comprises a plurality of polypeptide-encoding sequences bound to one or more unique detection tags, thereby creating a tagged nucleic acid library encoding a tagged polypeptide library,
      wherein the one or more unique detection tags comprise nucleotide sequences encoding polypeptide sequences, wherein one or more polypeptide detection tags are generated when the one or more unique detection tags are expressed;
   b. creating a database comprising a plurality of predicted mass spectrometry fragmentation patterns for each detection tag of the one or more detection tags bound to the plurality of polypeptide-encoding sequences, the plurality of predicted mass spectrometry fragmentation patterns being based on the one or more unique detection tags in isolation and on the polypeptide detection tags;
   c. expressing the tagged polypeptide library from the tagged nucleic acid library;
   d. selecting a tagged polypeptide from the tagged polypeptide library in a selection step;
   e. separating the one or more polypeptide detection tags from the selected tagged polypeptide, yielding one or more isolated detection tags;

f. identifying the one or more isolated detection tags by generating a fragmentation pattern of the one or more isolated detection tags by mass spectrometry; and g. matching the fragmentation pattern with one of the pluralities of predicted mass spectrometry fragmentation patterns, wherein the matching predicted mass spectrometry fragmentation pattern corresponds to the one or more isolated detection tags, thereby identifying the selected polypeptide.

2. The method of claim 1, wherein the molecular mass of the one or more unique detection tags is between 500 and 2500 Da.

3. The method of claim 1, wherein the molecular mass of one or more unique detection tags is between 900 and 2200 Da.

4. The method of claim 1, wherein the one or more isolated detection tag(s) is characterized by a hydrophobicity value of between−27 and 128.

5. The method of claim 1, wherein the one or more isolated detection tag(s) is characterized by a hydrophobicity value of between−1 and 70.

6. The method of claim 1, wherein one or more isolated detection tag(s) comprises a sequence element I selected from a collection of sequence elements I, wherein the sequence element I consists of 5 to 10 amino acids independently of each other selected from A, S, T, N, Q, D, E, V, L, I, F, Y, W, G and P.

7. The method of claim 6, wherein the sequence element I consists of 7 amino acids independently of each other selected from A, S, T, N, Q, D, E, V, L, I, F, Y, W, G and P.

8. The method of claim 1, wherein the one or more isolated detection tag(s) consists of a sequence element III which is GS, the sequence element I consisting of 5 to 10 amino acids independently of each other selected from A, S, T, N, Q, D, E, V, L, I, F, Y, W, G and P, and a sequence element II selected from SEQ ID NO 01 (WR), SEQ ID NO 02 (WLR), SEQ ID NO 03 (WQSR), SEQ ID NO 04 (WLTVR) and SEQ ID NO 05 (WQEGGR), wherein in particular the order of the sequence elements from N-terminus to C-terminus is the sequence element III, the sequence element I, the sequence element II.

9. The method of claim 1, wherein a selection criteria of the selection step is selected from the group consisting of: an ability to bind to a target molecule with a defined affinity, stability of a polypeptide at defined conditions, a certain aggregation behavior at defined conditions, resistance towards proteases, tissue penetration abilities, fast or slow clearance from the blood stream, an ability to penetrate the blood-brain-barrier, and an ability to accumulate in tumors.

10. A mass spectrometry fragmentation based method for selecting a polypeptide from a library of polypeptides, comprising:

a. deep sequencing a tagged nucleic acid library comprising a plurality of polypeptide-encoding sequences each bound to one or more unique detection tags, wherein the one or more unique detection tags comprise nucleotide sequences encoding corresponding unique polypeptide sequences, wherein one or more unique polypeptide detection tags are generated when the one or more unique detection tags are expressed;

b. creating a database comprising a plurality of predicted polypeptide mass spectrometry fragmentation patterns for each detection tag of the one or more detection tags bound to of the plurality of polypeptide-encoding sequences, the plurality of predicted mass spectrometry fragmentation patterns being based on the one or more unique detection tags in isolation and on the polypeptide detection tags;

c. expressing the tagged polypeptide library from the tagged nucleic acid library, thereby generating a plurality of polypeptides each bound to one or more unique polypeptide detection tags;

d. selecting a tagged polypeptide from the tagged polypeptide library in a selection step, yielding a selected tagged polypeptide;

e. separating the one or more unique polypeptide detection tags from the selected tagged polypeptide, yielding one or more unique isolated detection tags;

f. identifying the one or more unique isolated polypeptide detection tags by generating a fragmentation pattern of the one or more unique isolated polypeptide detection tags by mass spectrometry;

g. matching the fragmentation pattern of the one or more unique isolated polypeptide detection tags with a corresponding predicted polypeptide mass spectrometry fragmentation pattern from the predicted polypeptide mass spectrometry fragmentation patterns created in step b., thereby identifying the one or more unique isolated polypeptide detection tags; and h. selecting, from the tagged nucleic acid library one or more sequences encoding the one or more unique isolated polypeptide detection tags bound to the corresponding polypeptide-encoding nucleic acid sequence, thereby selecting a polypeptide library of polypeptides.

11. The method according to claim 10, wherein the molecular mass of the detection tag is between 500 and 2500 Da.

12. The method according to claim 10, wherein the molecular mass of the detection tag is between approximately 900 and 220 Da.

13. The method according to claim 10, wherein each member of the polypeptide library or each detection tag is associated with an affinity tag, wherein the affinity tag is selected from the group comprising a His-tag, a CBP-tag, a CYD-tag, a Strep-tag, a StrepII-tag, a FLAG-tag, a HPC-tag, a GST-tag, an Avi-tag, a biotinylation tag, a Myc-tag, a 3xFLAG tag and a MBP-tag, and/or, wherein the affinity tag is separated from the detection tag by a second severable element, and the second severable element is severed prior to identifying the isolated detection tag.

14. The method of claim 13, wherein a selection criteria of the selection step is selected from a group of criteria consisting of: an ability to bind to a target molecule with a defined affinity, stability of a polypeptide at defined conditions, a certain aggregation behavior at defined conditions, resistance towards proteases, tissue penetration abilities, fast or slow clearance from the blood stream, an ability to penetrate the blood-brain-barrier, or an ability to accumulate in tumors.

15. A mass spectrometry fragmentation based method for selecting a polypeptide from a library of polypeptides, comprising:

a. generating a tagged nucleic acid library encoding a tagged polypeptide library comprising a plurality of library members that each comprises a polypeptide and a detection tag, which are separated by a first severable element;

b. deep sequencing the tagged nucleic acid library encoding the tagged polypeptide library comprising the plurality of library members, thereby obtaining a plurality of nucleic acid sequences from the tagged nucleic acid library;

c. creating a database comprising a plurality of predicted mass spectrometry fragmentation patterns by predicting a predicted fragmentation pattern by mass spectrometry for each of a plurality of detection tags encoded by a tag-encoding sequence from the plurality of nucleic acid sequences, the plurality of predicted mass spectrometry fragmentation patterns based on the one or more unique detection tags in isolation;

d. expressing the tagged polypeptide library from the tagged nucleic acid library;

e. selecting a selected polypeptide from the tagged polypeptide library;

f. severing the first severable element, thereby yielding an isolated detection tag;

g. identifying the isolated detection tag by generating a fragmentation pattern of the isolated detection tag by mass spectrometry and matching the fragmentation pattern with the plurality of predicted mass spectrometry fragmentation patterns; and h. choosing from the plurality of nucleic acid sequences a nucleic acid sequence comprising an isolated tag-encoding sequence encoding the isolated detection tag, thereby selecting a tagged polypeptide member of the tagged polypeptide library associated with the isolated detection tag.

16. The method of claim 15, wherein the isolated detection tag comprises a sequence element I selected from a collection of sequence elements I, wherein the sequence element I consists of 5 to 10 amino acids independently of each other selected from A, S, T, N, Q, D, E, V, L, I, F, Y, W, G and P.

17. The method of claim 16, wherein the sequence element I consists of 7 amino acids independently of each other selected from A, S, T, N, Q, D, E, V, L, I, F, Y, W, G and P.

18. The method of claim 15, wherein the isolated detection tag consists of a sequence element III which is GS, the sequence element I consisting of 5 to 10 amino acids independently of each other selected from A, S, T, N, Q, D, E, V, L, I, F, Y, W, G and P, and a sequence element II selected from SEQ ID NO 01 (WR), SEQ ID NO 02 (WLR), SEQ ID NO 03 (WQSR), SEQ ID NO 04 (WLTVR) and SEQ ID NO 05 (WQEGGR), wherein in particular the order of the sequence elements from N-terminus to C-terminus is the sequence element III, the sequence element I, the sequence element II.

19. The method of claim 15, wherein a selection criteria of the selection step is selected from a group of criteria consisting of: an ability to bind to a target molecule with a defined affinity, stability of a polypeptide at defined conditions, a certain aggregation behavior at defined conditions, resistance towards proteases, tissue penetration abilities, fast or slow clearance from the blood stream, an ability to penetrate the blood-brain-barrier, or an ability to accumulate in tumors.

20. The method of claim 1, wherein the selection step in step d. further comprises the application of a selection pressure to the tagged polypeptide library to form a physically separated sub-pool of one or more selected tagged polypeptides.

* * * * *

UNITED STATES PATENT AND TRADEMARK OFFICE
CERTIFICATE OF CORRECTION

PATENT NO. : 12,054,708 B2
APPLICATION NO. : 16/345895
DATED : August 6, 2024
INVENTOR(S) : Markus Seeger It is certified that error appears in the above-identified patent and that said Letters Patent is hereby corrected as shown below:

In the Specification

Column 8, Line 7, delete "library" and insert -- library. --.

Column 9, Line 47, delete "$\leq 5\times$." and insert -- $\geq 5\times$. --.

Column 19, Line 32, delete "Illumine" and insert -- Illumina --.

Column 21, Line 56, delete "Illumine" and insert -- Illumina --.

Column 25, Line 55, delete "(MBP)" and insert -- (MBP). --.

Column 26, Line 26, delete "Illumine" and insert -- Illumina --.

Column 26, Line 47, delete "searches" and insert -- searches. --.

Column 27, Line 61, delete "Illumine" and insert -- Illumina --.

Column 33, Line 27, delete "µg" and insert -- pg --.

In the Claims

Column 37, Line 19, Claim 4, delete "between–27" and insert -- between -27 --.

Column 37, Line 22, Claim 5, delete "between–1" and insert -- between -1 --.

Column 37, Line 66, Claim 10, after "to" delete "of".

Column 38, Line 25, Claim 10, delete "library" and insert -- library, --.

Signed and Sealed this
Twelfth Day of November, 2024

Katherine Kelly Vidal
*Director of the United States Patent and Trademark Office*